US007486166B2

(12) United States Patent
Humphries et al.

(10) Patent No.: US 7,486,166 B2
(45) Date of Patent: Feb. 3, 2009

(54) HIGH PERFORMANCE HYBRID MAGNETIC STRUCTURE FOR BIOTECHNOLOGY APPLICATIONS

(75) Inventors: David E. Humphries, El Cerrito, CA (US); Martin J. Pollard, El Cerrito, CA (US); Christopher J. Elkin, San Ramon, CA (US)

(73) Assignee: The Regents of the University of California, Oakland, CA (US)

( * ) Notice: Subject to any disclaimer, the term of this patent is extended or adjusted under 35 U.S.C. 154(b) by 16 days.

(21) Appl. No.: 11/595,827

(22) Filed: Nov. 9, 2006

(65) Prior Publication Data

US 2007/0182517 A1 Aug. 9, 2007

Related U.S. Application Data

(63) Continuation-in-part of application No. 11/248,934, filed on Oct. 11, 2005, now Pat. No. 7,148,778, which is a continuation-in-part of application No. 10/305,658, filed on Nov. 26, 2002, now Pat. No. 6,954,128.

(60) Provisional application No. 60/335,226, filed on Nov. 30, 2001.

(51) Int. Cl.
*H01F 7/02* (2006.01)
*G01N 33/553* (2006.01)

(52) U.S. Cl. ...................................... 335/306; 436/526

(58) Field of Classification Search ......... 335/210–213, 335/302–306; 210/222, 695; 436/526
See application file for complete search history.

(56) References Cited

U.S. PATENT DOCUMENTS 3,398,315 A * 8/1968 Washburn ................... 315/3.5
4,742,271 A * 5/1988 MacMaster et al. ........ 315/39.3

* cited by examiner

*Primary Examiner*—Ramon M Barrera
(74) *Attorney, Agent, or Firm*—Fulbright & Jaworski LLP

(57) ABSTRACT

The present disclosure provides a high performance hybrid magnetic structure made from a combination of permanent magnets and ferromagnetic pole materials which are assembled in a predetermined array. The hybrid magnetic structure provides means for separation and other biotechnology applications involving holding, manipulation, or separation of magnetic or magnetizable molecular structures and targets. Also disclosed are further improvements to aspects of the hybrid magnetic structure, including additional elements and for adapting the use of the hybrid magnetic structure for use in biotechnology and high throughput processes.

17 Claims, 21 Drawing Sheets

HIGH PERFORMANCE HYBRID MAGNETIC STRUCTURE FOR BIOTECHNOLOGY APPLICATIONS

CROSS-REFERENCE TO RELATED APPLICATIONS

This application claims priority to and is a continuation-in-part of U.S. patent application Ser. No. 11/248,934, filed Oct. 11, 2005, now U.S. Pat. No. 7,148,778 which is a continuation-in-part of U.S. Ser. No. 10/305,658, filed Nov. 26, 2002, now U.S. Pat. No. 6,954,128, which claims priority from U.S. Provisional Application No. 60/335,226, filed Nov. 30, 2001, each of which are hereby incorporated by reference in their entirety.

STATEMENT OF GOVERNMENTAL SUPPORT

This invention was made during work supported by U.S. Department of Energy under Contract No. DE-AC03-76SF00098, now DE-AC02-05CH11231. The government has certain rights in this invention.

BACKGROUND OF THE INVENTION

1. Field of the Invention

The present invention relates to magnetic separation, concentration and other biotechnology applications involving holding, concentration, manipulation or separation of magnetic or magnetizable molecular structures and targets.

2. Background of the Related Art

There are two common types of magnet materials: permanent magnets and ferromagnetic materials. The following is brief background on ferromagnetic and permanent magnetic materials and their use in hybrid magnets.

Permanent Magnets

Permanent magnets are anisotropic or "oriented" materials which have a preferred magnetization axis. When they are magnetized they produce magnetic fields that are always "on" (e.g. they will stick to your refrigerator). The distribution of these fields is dependent upon the "orientation" of the material, its geometry and other material properties. Permanent magnetic material should be distinguished from paramagnetic materials, which are magnetic materials, such as aluminum, that exhibit no magnetic properties in the absence of a magnetic field. Permanent magnets consist of both paramagnetic components, e.g., samarium, neodymium, and ferromagnetic components, e.g., iron, cobalt. During fabrication a crystalline domain structure is created which exhibits spontaneous oriented intra-domain magnetization known as magneto-crystalline anisotropy. This anisotropy is the mechanism that produces strong fields in current rare-earth permanent magnets.

Proprietary processes involving compression of finely pulverized component particles in a strong, ambient magnetic field, sintering of the compressed material and finally remagnetization in a second strong ambient field are used to produce these materials. Once magnetized, these materials will keep these fields indefinitely. However, damage by heating will reduce or eliminate the magnetism.

Soft Ferromagnetic Materials

Soft ferromagnetic materials are macroscopically isotropic or non-oriented. When they have not been exposed to an external magnetic field they produce no magnetic field of their own. These materials include pure iron, common low-carbon steel alloys and more exotic materials such as vanadium permendur which is composed of iron, cobalt and vanadium. The importance of these materials is that they will tend to concentrate and redirect magnetic flux from other sources such as electromagnetic coils or permanent magnets.

Soft ferromagnetic materials typically have some component of iron or other transition metals and include pure iron or alloys of steel. For example, steel that does not evidence magnetism is a macroscopically isotropic material, i.e., has no intrinsic orientation in an annealed state, and is a magnetically malleable material. When exposed to a magnetic field from another source, soft ferromagnetic materials will tend to concentrate and make the field stronger and redirect the field.

Ferrimagnetic Materials

Ferrimagnetic materials are macroscopically similar to ferromagnetic materials but microscopically, ferrimagnetic materials exhibit an anti-parallel alignment of unequal atomic moments. The imbalance in moments is caused by the presence of Fe ions with different oxidation states. This results in a non-zero net magnetization. The magnetic response to an external magnetic field is therefore large but smaller than that for a ferromagnetic material. Thus this material exhibits susceptibility to an applied external field but when the external field is removed, no appreciable remnant field exists in the material because of the weak nature of the magnetic moments of the coupled atoms.

Hybrid Magnets

Hybrid magnets use both permanent magnets and soft ferromagnetic materials. A comprehensive theory of hybrid structures was formulated by Dr. Klaus Halbach for accelerator applications. Combining permanent and soft ferromagnetic materials to form a hybrid magnet became a well-known method in the free electron laser and particle accelerator community, fields unrelated to the present field of use. Such hybrid magnet configurations are used in insertion devices, such as undulators and wigglers, which are used in accelerators that produce high-energy particle beams. Typically very large and powerful magnets are used to accelerate and/or influence particle behavior, causing particles that are exposed to the magnetic fields to "wiggle" or "undulate." This transverse motion is caused by the Lorentz force effect. See Halbach, U.S. Pat. No. 4,761,584, which discloses a "Strong permanent magnet-assisted electromagnetic undulator" and Halbach, U.S. H450, which discloses a "Magnetic field adjustment structure and method for a tapered wiggler."

The field gradient structure is created by the combination of linear permanent magnets and specially shaped soft ferromagnetic steel poles. The gradient distributions of these hybrid structures can be controlled and shaped to produce both vertical and horizontal fine-scaled gradients. The forces on magnetic materials are created by these gradients in the field produced by these hybrid structures.

The typical insertion device has magnets arranged in two opposed rows. Each row alternates soft ferromagnetic pole pieces with blocks of permanent magnet material. The magnetic fields of each block of permanent magnet material are oriented orthogonal to the magnetic field orientation of the soft ferromagnetic poles and in the opposite direction of the next block of permanent magnet material. A particle beam is passed along the rows in the space between the two opposing rows. The alternating magnetic orientations along the direction of travel of the particle beam produce precise periodic magnetic fields and cause the particle beam to follow a periodic path or an undulating orbit.

The soft ferromagnetic poles, sometimes referred to as steel poles, can be made from a variety of materials, ranging from exotic materials such as vanadium permendur, which result in better and higher performance magnets, to cheaper materials such as low-carbon steel. Examples of permanent magnet are rare-earth cobalt magnets, such as SmCo magnets, and Neodymium Iron and Boron (NdFeB) magnets.

The permanent magnets act as magnetic flux generators and the soft ferromagnetic poles act as concentrators to produce higher fields with distributions that are more easily controlled. This is called an "iron-dominated" system, i.e., the field distributions in the regions of interest are primarily controlled by the soft ferromagnetic pole geometry and material characteristics rather than the permanent magnets.

Use of Magnetic Devices in Biological Applications

The high performance hybrid magnetic structure herein described relates generally to apparatus and methods for biotechnology applications involving holding, concentration, manipulation or separation of magnetizable molecular structures and targets. The use of magnets in the biological applications involving such techniques as purifying and concentrating molecular particles, separation and concentration of specific targets and ligands for identification of biological pathogens and other molecular particles, has become increasingly popular and widely used. This technique typically involves the immobilization or attachment of the target or structure in a mixture to a magnetic bead. The beads are then separated from the mixture by exposure to a magnetic field. After the structures and targets are released from the beads, the structures and targets can then be used for further applications, testing or identification.

The magnetic beads or particles are, or typically contain, ferrimagnetic material. Magnetic beads may range in diameter from 50 nm (colloidal "ferrofluids") to several microns. The magnetic beads used in some molecular separation systems contain iron-oxide materials which are examples of ferrimagnetic materials. These beads experience a force in a gradient field but do not retain a remnant magnetic field upon removal of the external gradient field and thus are not attracted to each other. This mechanism allows the beads to disperse in solution in the absence of a magnetic field, but be attracted to each other in the presence of a magnetic field.

Many companies, including Dynal, have developed biological (e.g. antibody-, carboxylate-, or streptavidin-coated) and chemically activated (e.g. Tosyl group or amino group) magnetic particles to aid researchers in developing novel approaches to assay, identify, separate or purify biological particles from heterogeneous or homogenous solutions.

Hybrid magnetic technology has been widely known and used in the accelerator community, however, it has not been applied to any biotechnology application thus far. Commercial methods of magnetic separation, currently in industry use, have been "permanent magnet dominated" systems. This means that the field distributions are controlled by the geometry and orientations of the permanent magnets that are in the plates. Previous technology produces weak fields and gradients that give poorer results and long separation times.

In some cases the current usage of soft ferromagnetic materials is mainly as a magnetic shield, rarely as a means of concentrating the magnetic field. Howe et al., U.S. Pat. No. 5,458,785, disclose a magnetic separation method using a device which incorporates ferromagnetic material as a base and as a field concentrator plate overlying the permanent magnet material that are of alternating magnetic orientation. The differences are readily apparent when cross-sections of the two magnetic structures are compared. The fundamental magnetic circuits of the two structures are different. The design as shown by Howe et al. is limited in terms of field increases from vertical scaling. Any change in the dimensions of each component of the structure vertically or horizontally, changes the field in the region of interest. Furthermore, the fundamental design of the Howe magnetic structure is not capable of producing the level of field strength that can be produced by the current invention.

Li et al. disclose in U.S. Pat. No. 4,988,618, a magnetic separation device using rare earth cobalt magnets spaced equidistant surrounding the wells in a 96-well plate. All the permanent magnets are oriented coplanar to the base and are either uni-directionally or in alternate directions from the next permanent magnet. Yu, in U.S. Pat. No. 5,779,907, discloses a similar apparatus wherein the magnets are positioned in the spaces between the wells of the microplate. Chen et al., in U.S. Pat. No. 6,036,857, disclose an apparatus for continuous magnetic separation of components from a mixture, wherein the magnets are arranged in alternating magnetic orientations, either aligned side-by-side or alternatively slightly offset from each other magnet.

Manufacturers and Suppliers of Magnetic Plates and Separation Devices or Kits

A majority of the magnet plates that are commercially available are made to be used in conjunction with industry standard microtiter plates. The following are examples of major manufacturers and suppliers of magnetic plates and separations devices or kits.

Agencourt Bioscience Corporation (Beverly, Mass.) produces two types of magnetic plates. Available are a 96-magnet plate having ring-shaped permanent magnets and a 96-magnet plate having disc-shaped permanent magnets. The ring-shaped magnets are of the right dimension to allow the wells of a 96-well microtiter plate to fit inside the ring, encircled by the magnet. Magnet plates having ring-shaped permanent magnets are widely used because they are readily available from manufacturers such as Atlantic Industrial Mottels (20 Tioga Way, Marblehead, Mass.) which produces a 96-well "donut" magnet plate. The availability and low cost of these magnets also make assembly of a magnet plate fairly easy and at low cost to the user.

The magnet plate available from Promega, Inc. (Madison, Wis.) uses 24 paramagnetic pins to draw silica magnetic particles (See U.S. Pat. No. 6,027,945 which discloses this method) to the sides of the wells in a thermal cycling plate. An aluminum holder that centers the magnet plate in a robotic platform is also available. A similar pin magnet is also available.

PROLINX, Inc. (Bothell, Wash.) also produces magnetic plates having bar magnets for use with 96-well and 384-well microtiter plates. These magnetic plates hold strips or rectangular block-shaped strong permanent magnets which are placed lengthwise to exert a field on the columns of 96- or 384-well microtiter plates.

Dynal Biotech (Lake Success, N.Y.), which also produces super paramagnetic particles, makes several magnetic plates for use with microcentrifuge tubes and 96-well microtiter plates. Their magnetic plates are made from disinfectant proof polyacetate equipped with rare earth Neodymium-Iron-Boron permanent magnets.

BRIEF SUMMARY OF THE INVENTION

The present invention provides a high performance hybrid magnetic structure, made from a combination of permanent magnets and soft ferromagnetic materials, useful for separation and other biotechnology applications involving holding, manipulation, or separation of magnetic or magnetizable molecular structures and targets.

The hybrid magnetic structure is generally comprised of: a non-magnetic base, a ferromagnetic pole having a shaped tip extending in height to a bottom edge, at least two blocks of permanent magnet material, assembled onto the base, on opposite sides of and adjacent to the ferromagnetic pole in a periodic array, and having the magnetization orientations of the blocks oriented in opposing directions and orthogonal to the height of the ferromagnetic pole. The blocks of permanent magnet material should extend below the bottom edge of the ferromagnetic pole when assembled onto the base. The hybrid magnetic structure can further comprise two ferromagnetic poles, one on each end of said periodic array.

The hybrid magnetic structure preferably further comprises at least one retainer adjacent the outermost block of magnetic material and even more preferably a pair of opposing retainers extending orthogonally to the magnetization orientation of the blocks of permanent magnet material.

The hybrid magnetic structure should have a magnetic field strength of at least 6000 Gauss, preferably 8000 Gauss, and even more preferably a magnetic field strength of 1 Tesla.

The non-magnetic base is preferably a non-magnetic material such as aluminum.

The ferromagnetic pole should be made of soft ferromagnetic materials such as steel, low-carbon steel or vanadium pemendur. The pole tip of the ferromagnetic pole can be shaped to create unique field gradients. The pole tip can be of any shape, which in cross section is preferably a trapezoid, T-shaped, inverted L-shaped, circle, triangle, elliptical, conical, or a polyhedron such as a square, rectangle, trapezium, rhombus, and rhomboid, or any shape depending on the desired field gradient distribution to be produced.

The pole tip can be shaped to be in close proximity with a containment vessel to be acted on. The improvement comprising an asymmetric pole tip, featuring notches at various points along the pole length or between well cut-outs to increase the field strength that liquid containers, such as microplate wells, are exposed to from the hybrid structure. The notches approach but do not pass the center line of the pole.

In another aspect, the ferromagnetic pole features a chamfer, i.e., angled surface, to allow the liquid container to come into close proximity or contact with the hybrid magnetic structure. The chamfer may be of any applicable size or width, thus allowing the pole to contour the shape of the liquid container(s) if desired. The chamfer may also serve to seat the liquid container securely to the hybrid magnetic structure, to smooth any sharp edges for safety, or to seat an upper interface or attachment used to securely seat any multi-well container onto the hybrid magnetic structure.

In another embodiment, a long period hybrid magnetic structure featuring well cutouts in the ferromagnetic poles and retainer rods to hold the assembly together. The periodicity is doubled to achieve two-fold extension of the fields for deep well containment vessel applications. Circular cutouts in the poles and blocks can be made to fit retainer rods through so the retainer rods can be secured to the retainers through a fastening means. The retainer rods are preferably inserted through a section of the pole having less or unsaturated flux so as not to interfere with the internal flux distribution and inadvertently decrease performance and gradient strength.

In one aspect, the ferromagnetic poles are periodically uniform wedge poles. In another aspect, the ferromagnetic poles are non-uniform wedges to create compactness in the hybrid magnetic structure and for tuning of the field distribution for periodic and non-periodic effects.

The blocks of permanent magnet material are preferably comprised of a rare earth element, such as neodymium iron boron or samarium cobalt. The blocks of permanent magnet material should extend beyond the ends and below the bottom edges of the ferromagnetic poles. The blocks of permanent magnet material can be assembled having the magnetization orientation of the blocks oriented in opposing directions and orthogonal to the height of the ferromagnetic pole.

In one aspect, an improvement comprising lower blocks of permanent magnet material inserted below a ferromagnetic pole to increase or decrease the field strength at a specific pole from 0-15% depending on the size of the block. If the magnetization orientation of the lower block of permanent magnet material should face in the same direction relative to the pole, i.e., in or out, as the magnetization orientations of all blocks of permanent magnet material around that pole piece, then the field strength will be increased at that pole. If the magnetization orientation of the lower block of permanent magnet material should face in the opposite direction relative to the pole as the magnetization orientations of all blocks of permanent magnet material around that pole piece, then the field strength will be decreased at that pole.

One embodiment of the hybrid magnetic structure is intended for use in conjunction with most industry standard microtiter plate formats including 96-, 384- and 1536-well plates. The hybrid magnetic structure can further comprise an upper interface attached on top of the hybrid magnetic structure, and a microtiter plate on the hybrid magnetic structure so that the microtiter wells in the microtiter plate are disposed between the ferromagnetic poles. The hybrid magnetic structure can further comprise a lower locator plate attached to the bottom of the hybrid magnetic structure.

The field strengths of selected poles and the hybrid magnetic structure can be improved by a return yoke. In one embodiment, the return yoke is a flux conduit having sufficient cross section to avoid saturation and wherein the return yoke is sufficient distance from the bottom of the hybrid magnetic structure to avoid significant magnetic interaction. In another embodiment, the return yoke is a shield to minimize strong fields below the hybrid magnetic structure.

The hybrid magnetic structure can further comprise a protective cover which magnetically attaches to the top of the magnetic structure to prevent unwanted interaction with another hybrid magnetic structure or magnetic material and to provide a surface for warning against bodily injury.

In another embodiment of the hybrid magnetic structure, having a field strength of greater than 6000-8000 Gauss, comprising: a non-magnetic base having grooves therein; a ferromagnetic pole having a shaped tip extending in height to a bottom edge; at least two blocks of permanent magnet material, assembled onto said base and extending into said grooves, on opposite sides of and adjacent to the ferromagnetic pole.

Another embodiment of the hybrid magnetic structure comprises: a non-magnetic base having grooves therein; a T-shaped ferromagnetic pole, wherein the "T" is opposite the base end; at least two blocks of permanent magnet material, assembled onto the base, wherein the T-shaped ferromagnetic pole is assembled onto the base between the blocks of permanent magnet material in a periodic array, with each block of permanent magnet material having a magnetization orientation which is oriented in an opposing direction to each adjacent permanent magnet and orthogonal to a lateral plane of the ferromagnetic pole; and two inverted L-shaped ferromagnetic poles, one on each end said of said periodic array of T-shaped ferromagnetic pole and blocks of permanent magnet material.

A radially arranged hybrid magnetic structure comprises: a non-magnetic base having grooves extending from a center point therein; a wedge-shaped ferromagnetic pole having a bottom edge and tapered towards the center; at least two wedge-shaped blocks of permanent magnet material, assembled onto the base, wherein the wedge-shaped ferromagnetic pole is radially or circumferentially assembled onto the base between the blocks of permanent magnet material in a periodic array, with each block of permanent magnet material having a magnetization orientation which is oriented in an opposing direction to each adjacent permanent magnet and orthogonal to a lateral plane of the wedge-shaped ferromagnetic pole. The radially-arranged hybrid magnetic structure can further comprise a lower block of permanent magnet material assembled onto the base at the bottom edge of the ferromagnetic pole, wherein the magnetization orientation of the lower block of permanent magnet material is oriented axially facing into or out of the ferromagnetic pole, and wherein the magnetization orientations of the blocks of permanent magnet material and the lower blocks of permanent magnet material are all facing into or out of the ferromagnetic pole.

Another embodiment of the hybrid magnetic structure comprises: a non-magnetic base having grooves therein; a annular ferromagnetic pole; at least two annular blocks of permanent magnet material, assembled onto said base, wherein the annular ferromagnetic pole is assembled onto the base between the annular blocks of permanent magnet material in a periodic array, with each block of permanent magnet material having a magnetization orientation which is oriented in an opposing direction to each adjacent permanent magnet and orthogonal to a lateral plane of the annular ferromagnetic pole.

The invention further comprises a method of separating magnetized molecular particles from a sample, comprising the steps of: (a) placing the sample containing the magnetized molecular particles in close proximity with a hybrid magnetic structure, whereby there is formed a region comprising concentrated magnetized molecular particles; (b) removing supernatant liquid without disturbing the region; (c) removing the vessel from close proximity with said hybrid magnetic structure; and (d) re-suspending the magnetized molecular particles in a liquid, wherein the hybrid magnetic structure comprises a non-magnetic base; blocks of permanent magnet material; and a ferromagnetic pole having a bottom edge and a shaped tip; wherein the tip is adjacent to the sample during separation. The magnetic field strength should be at least 6000 Gauss, preferably 8000 Gauss, and even more preferably a magnetic field strength of 1 Tesla.

The method can be directed to at least 96 samples that are separated in parallel, wherein the samples contain DNA coupled to a ferrimagnetic material. The method is also directed toward samples that contain a ferrimagnetic material coupled to a biological material including but not limited to polynucleotides, polypeptides, proteins, cells, bacteria, and bacteriophage.

BRIEF DESCRIPTION OF THE DRAWINGS

FIG. 11 shows different embodiments of the hybrid magnetic structure.

FIG. 12 shows a hybrid magnetic structure featuring well cutouts and notches in an asymmetric ferromagnetic pole. FIG. 12B.1 and 12B.2 show the length of the pole from two different perspective views. FIG. 12B.3 is a top view of the pole to show the well cutouts and notches. FIG. 12B.4 is a cross-sectional view of the pole to show the shape of the tip is asymmetric.

FIG. 13 shows a long period hybrid magnetic structure featuring well cutouts in the ferromagnetic pole and retainer rods to hold the assembly together.

DESCRIPTION OF THE PREFERRED EMBODIMENT

Definitions

Figure 1:
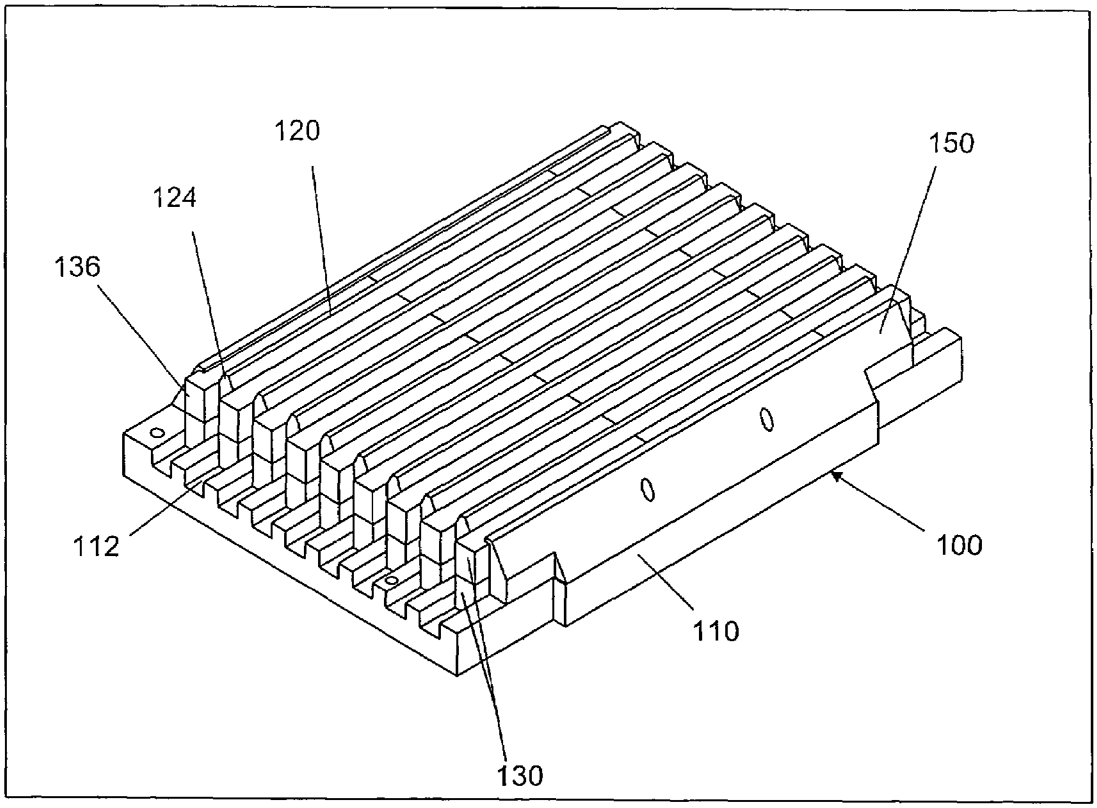
FIG. 1 is a perspective view of the preferred hybrid magnetic structure.

"Permanent magnets" and "permanent magnet materials" herein refers to anisotropic or "oriented" materials which have a preferred magnetization axis. When these materials are magnetized, they produce magnetic fields that are always "on".

"Ferromagnetic poles," "soft ferromagnetic poles," "pole (s)" and "pole pieces" as used herein refer to pieces or members, of any shape, made from soft ferromagnetic materials. Soft ferromagnetic materials are macroscopically isotropic or non-oriented. When these materials have not been exposed to an external magnetic field they produce no net magnetic field of their own.

"Hybrid magnets" as used herein refers to devices having a combination of permanent magnet material and soft ferromagnetic pole pieces, wherein the soft ferromagnetic pole pieces alternate in a periodic array with blocks of permanent magnet material. The magnetic fields of each block of permanent magnet material are oriented orthogonal to a lateral plane of the soft ferromagnetic poles and in the opposite direction of each adjacent block of permanent magnet material.

"Magnetization orientation," "anisotropic orientation" or "magnet(ic) orientation" as used herein refers to the magnetic orientation or a preferred magnetization axis of permanent magnet material.

"Field" or "field level" as used herein refers to the magnetic fields generated by the ferromagnetic and permanent magnet materials in the magnet structure. Fields are expressed in units of Gauss (G) or Tesla (T).

"High field(s)" as used herein refers to the magnetic fields generated above 0.6 Tesla or 6000 Gauss.

"Field gradient structure" as used herein refers to the shape of the magnetic field gradient produced by controlling the shape, size and number of ferromagnetic poles and the quantity and vertical dimension of the permanent magnet materials used in the hybrid magnetic structure.

"Geometric periodicity" as used herein refers to the distance or length over which the geometric pattern is repeated, specifically, the distance or length over which the geometric pattern of ferromagnetic poles and blocks of permanent magnet material is repeated. For example, the geometric periodicity of a preferred embodiment can be measured as the distance between the center of a first ferromagnetic pole tip and the center of the next adjacent pole tip or from the leading edge of a first ferromagnetic pole tip to the leading edge of the next adjacent pole tip.

"Magnetic Periodicity" refers to the periodic magnetic field created at the ferromagnetic pole tips and is typically twice the geometric period length.

"Microtiter plates" and "microplates" as used herein refer to industry-standard plastic plates that conform to a standard footprint size and that incorporate 96, 384 or 1536 wells that act as containers for various biological and chemical solutions. Microtiter plates are 8×12 arrays of 96 wells, 16×24 arrays of 384 wells and 32×48 arrays of 1536 wells. Microtiter plates that are used with magnet structures include "PCR" plates, that are made of materials such as polystyrene and have conically-shaped wells, and other available round or flat bottom well plates or blocks that are used as liquid containment vessels in biological applications.

"Orthogonal" as used herein refers to an orientation of about 90° in any direction from the reference angle or perpendicular at right angles.

"Longitudinal", "longitudinal direction", and "longitudinal axis" as used herein refers to a lengthwise or length dimension. For example, longitudinal axis of a ferromagnetic pole is an axis parallel to a lengthwise dimension as opposed to a width or height dimension of a magnetic pole.

"Blocks" as used herein refers to any desired shape of material including but not limited to, annular or partially annular, cylindrical, toroidal, helical, a triangular prism, a quadrangular prism, a hexagonal prism or any other polyhedron, T-shaped, and inverted L-shaped. These "blocks" have a cross-sectional area. Examples of preferred cross-sectional shapes include but are not limited to, square, rectangle, circle, elliptical, wedge, triangle, quadrilateral, and other polygons.

"Rare earth magnets" as used herein refer to permanent magnetic materials containing any of the rare earth elements (Elements 39, 57-71) such as neodymium or samarium.

INTRODUCTION

The present invention provides a high performance hybrid magnetic structure made from a combination of permanent magnets and ferromagnetic materials. The high performance hybrid magnetic structure is useful for separation and other biotechnology applications involving holding, manipulation or separation of magnetic or magnetizable molecular structures and targets. This hybrid magnetic structure is applicable to work in the broader fields of functional genomics and proteomics since it can be used for selective separation of molecular particles from cellular and other matter. In addition, the structure can be used in high-throughput drug development and other industrial processes requiring magnetic manipulation of dense arrays of samples in solution.

The hybrid magnetic structure can be used in conjunction with any magnetic beads or particles that are, or typically contain, ferromagnetic or ferrimagnetic material. Appropriate magnetic beads may range in diameter from 50 nm (colloidal "ferrofluids") to several microns. Many companies have developed biological (e.g. antibody-, carboxylate-, or streptavidin-coated) and chemically activated (e.g. Tosyl group or amino group) magnetic particles that would prove useful in magnetizing molecular structures and targets and thus then be acted upon by the hybrid magnetic structure. It is further contemplated that these magnetic particles can be the targets.

The combination of permanent magnet material and ferromagnetic poles creates a fine field gradient structure. This defining characteristic allows the hybrid magnetic structure to produce fields and gradients that are up to four times greater than previous industry-standard magnet plates and a more beneficial field distribution for a number of important applications. Special bonding fixtures may be needed to hold the magnets and mechanically restrain the components during assembly of the hybrid magnetic structure because of the high field strengths.

The hybrid magnetic structure can be adapted for use with a number of different microtiter plates and a variety of commercial liquid handling robots and other instruments including 96- and 384-channel liquid handling dispensers through the design and implementation of upper interfaces and lower locator plates. The hybrid magnetic structure may be adapted for use with other types of liquid containment vessels that are not microtiter plates, such as, for example round bottom test tubes or conical centrifuge tubes. Another embodiment of the hybrid magnetic structure may also be used for separation processes involving unpartitioned containers containing an entire solution that is acted upon, rather than individual wells containing different solutions. Other embodiments similar to those shown in FIGS. 11A-11D may be used for flow separation applications involving separation of magnetic or magnetized targets in fluids flowing in pipes, tubes and other liquid conduits.

A. Components and Materials of the General Embodiment

Referring now to FIG. 1, the component parts of the core assembly of a preferred embodiment of the hybrid magnetic structure, designated by general reference number 100, generally comprise: a non-magnetic base 110; a ferromagnetic pole 120; blocks of permanent magnet material 130.

Figure 3:
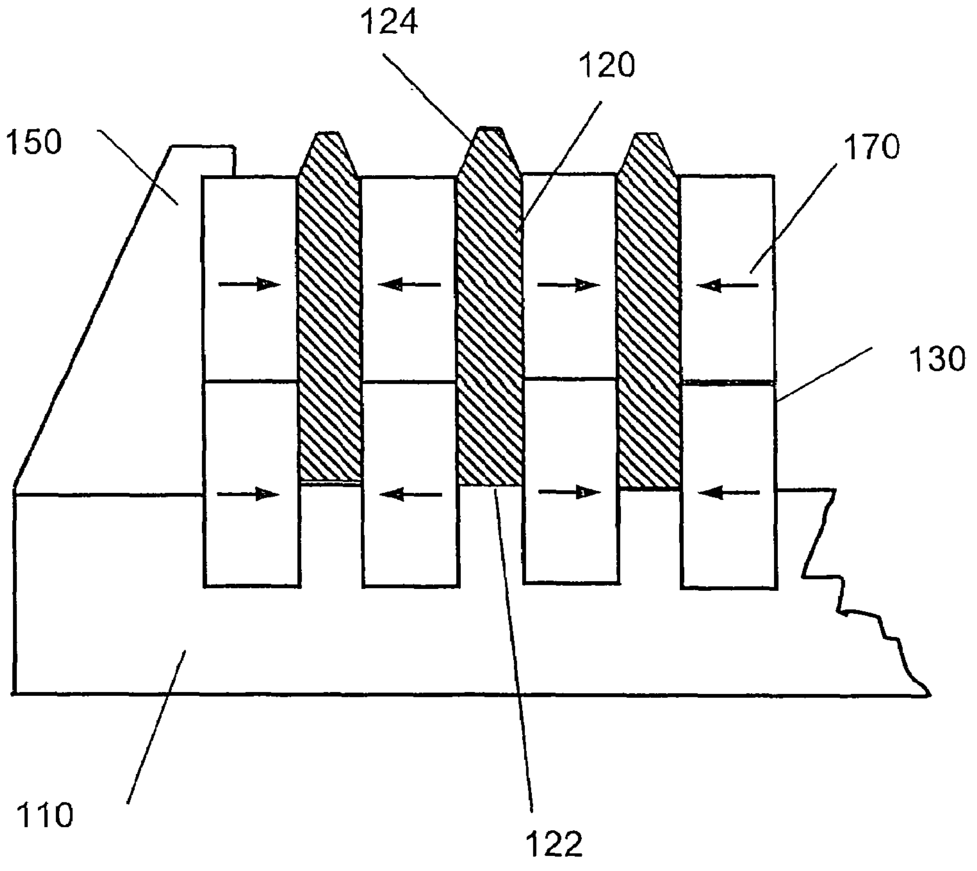
FIG. 3 is a cross-section of the preferred hybrid magnetic structure with magnet orientations of the permanent magnet material shown.

A ferromagnetic pole 120 is assembled onto the base 110 adjacent to a block of permanent magnet material 130 in a periodic array. The magnetic orientations 170 of each block of permanent magnet material are orthogonal to a lateral plane of the ferromagnetic poles 120, and in the opposite direction to that of each adjacent block of permanent magnet material 130. (FIG. 3).

Figure 2:
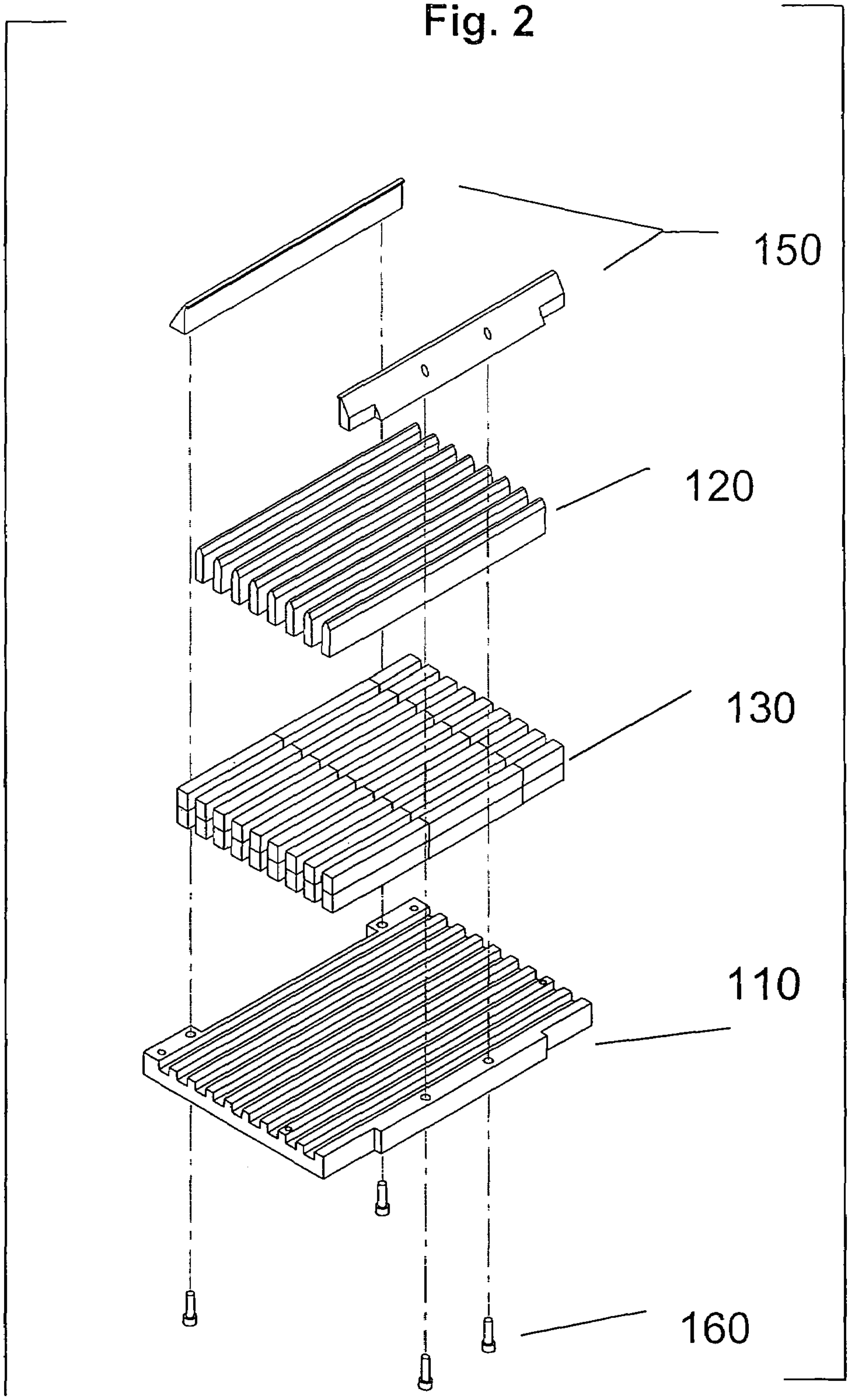
FIG. 2 is an exploded view of the preferred hybrid magnetic structure.

The block of permanent magnet material should extend below the bottom edge and beyond the length of the ferromagnetic pole. Grooves 112 can be machined into the base to seat the blocks of permanent magnet material below the bottom edge 122 and beyond the length of the soft ferromagnetic poles. A cross section of a preferred embodiment of the hybrid magnetic structure is shown with magnet orientations in FIG. 3 and an exploded view is shown in FIG. 2.

A preferred embodiment can further comprise a means for holding the base 110, ferromagnetic pole 120 and blocks of permanent magnet material 130 together by means of retainers 150 for the outboard magnets or a high strength bonding agent to hold components together. The retainers 150 and the non-magnetic base 110 would act as restraining mechanisms. Special shaping of the base and retainers can be done as well. Special shaping can be done for practical purposes to provide asymmetry so as to give a front side and a back side to the hybrid magnet structure. Alternatively, the base and retainers can be shaped to accommodate different shaped hybrid magnetic structures.

The soft ferromagnetic poles 120 can be fashioned from soft ferromagnetic material such as steel, low-carbon steel, vanadium pemendur, or other high-permeability magnetic material.

Permanent magnet materials 130 that are suitable for use in this invention are any oriented high field rare-earth materials and non-rare-earth materials such as hard-ferrites. Examples of preferred materials include, but are not limited to, rare-earth magnet materials, such as neodymium-iron-boron or samarium cobalt.

The performance of the hybrid magnetic structure is not dependent on a particular material but on the magnetic geometry and design. Materials can be exchanged and modified based on what kind of performance or cost parameters are set. Commercially available material can be ordered from industry vendors according to a specified shape and size.

The non-magnetic base means 110 can be made from any non-magnetic metal, high-strength composite or other non-magnetic material having sufficient mechanical properties, but preferably a material that is rigid, light and can be easily machined or molded. Examples of such suitable non-magnetic materials are: aluminum, a composite or plastic.

A non-magnetic base is recited and preferred, however, some embodiments may require a base comprised of ferromagnetic materials to be used as a shield to redirect stray magnetic fields away from the base. For example, if there is sensitive circuitry below the area whereupon the hybrid magnetic structure is placed, a base comprised of ferromagnetic materials should be used to redirect the magnetic fields up and away from the circuitry.

Figure 14:
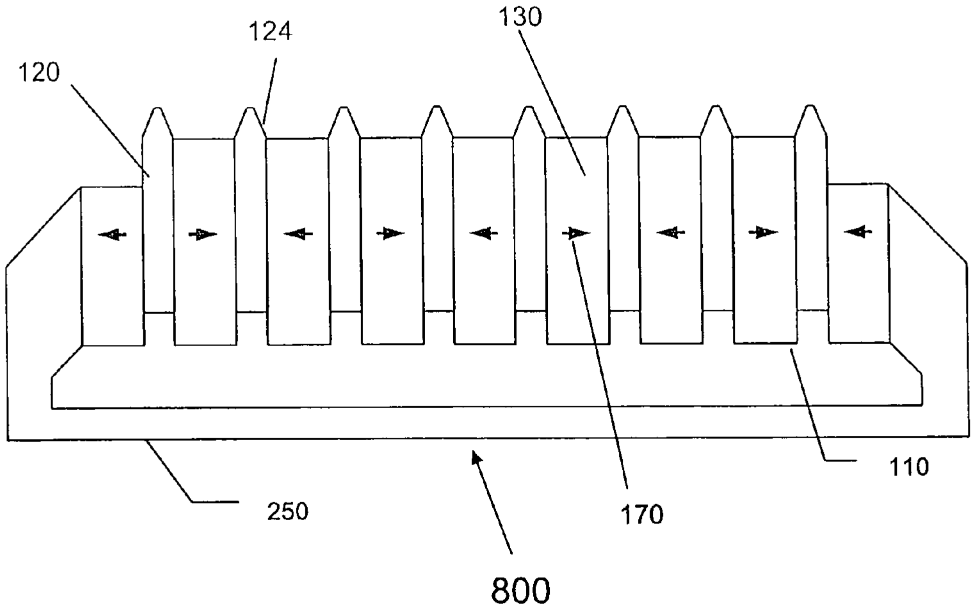
FIG. 14 shows a hybrid magnetic structure having a return yoke.

Alternatively, the hybrid magnetic structure can further comprise a return yoke to be used as a shield. Referring now to FIG. 14, a return yoke 250, made of a ferromagnetic material, preferably high permeability ferromagnetic steel, is assembled outside the non-magnetic base for shielding. The return yoke should be remote enough from the structure to avoid magnetic interaction, such as, shunting fields in the lower part of the structure or significantly perturbing field distributions in the main structure.

In another aspect, the return yoke 250 is a flux conduit to increase the field strengths of the outermost poles. If the return yoke is used as a flux conduit, the magnetization orientation 170 of outermost poles must be oriented in the same direction. The return yoke should cover the entire side surface area of the outermost poles and have sufficient thickness or cross-section extending out and down from the core of the structure to avoid saturation.

A person skilled in the art would appreciate that these structures experience high-magnitude internal forces during and after assembly and require a means for holding the base, pole pieces and permanent magnet material together. The hybrid magnetic structure components should be preferably bonded together because the internal forces are strong. It is preferred that a retainer and base system be fashioned, as the means for holding the base, ferromagnetic pole and blocks of high field permanent magnet material together, from non-magnetic metal or high-strength composite. Preferable bonding agents for application in this invention include unfilled epoxies having cured strengths greater than or equal to 2000 pounds per square inch. In one embodiment, if the structure is scaled up, retainer rods 140 can be used to hold the ferromagnetic pole(s), blocks of permanent magnet material and the retainers together. In a preferred embodiment, the retainer rods 140 are secured and the retainers 150 are preferably held to the base by means of fasteners 160. These fasteners 160 are generally non-magnetic stainless steel or other corrosion resistant material with similar mechanical characteristics.

Dimensions of a preferred embodiment used for applications involving 96-, 384- or 1536-well microtiter plates, are approximately 5.3 inches long by 3.7 inches wide by 1.1 inches tall, with a footprint slightly larger than a standard micro-titer plate. These dimensions vary with the particular specialized application of the hybrid magnetic structure. Therefore, the exact dimensions and configurations of the hybrid magnetic structure and the magnetic flux potentials are all considered to be within the knowledge of persons conversant with this art. It is therefore considered that the foregoing disclosure relates to a general illustration of the invention and should not be construed in any limiting sense.

B. Magnetic Circuit and Gradient Distributions (1) Magnetic Circuit

Some current users of magnetic devices in biological applications have tried to increase the field strength of their original designs by making a longer permanent magnet or simply stacking "donut-shaped" permanent magnets. None of these modifications will significantly increase a magnetic device's field strength. However, a feature of this hybrid magnetic structure is that the field strength can be increased by increasing the height of the permanent magnet material and the ferromagnetic poles. The hybrid magnetic structure is standalone and requires no external power source. It is powered solely by the magnetic circuit created by the permanent magnet material and the soft ferromagnetic poles.

As the height of the structure is increased, as in the case where the height of the poles from the bottom edge to the tip is increased, the flux density in the pole tips increases up to the limiting case where the pole tips reach their saturation point. For common magnet steels this saturation point is at approximately 17 kilo-Gauss. The implications are that the utilizable field levels for these magnetic structures can be close to that of saturation field level. In addition, because of the near-saturation condition in the magnet poles, the field gradients (and hence, the forces on magnetized particles) can be very strong.

As shown in FIG. 3, the permanent magnet material 130 is assembled with the magnetization orientation orthogonal to a lateral plane of the ferromagnetic poles and in opposing directions, to create a large pole-to-pole scalar potential difference that results in high magnetic flux density between the upper pole tips and a corresponding, alternating polarity.

The permanent magnet material 130 should extend below the bottom edges of the soft ferromagnetic poles 120 preferably into grooves 112 machined into base 110. The permanent magnet material 130 that extends below the bottom edge 122 of the poles inhibits the pole-to-pole flux and results in a reduced field at the lower surfaces of the magnetic structure. As such, it is important to incorporate this aspect of the hybrid magnetic structure into its design if the application uses only the upper surface of the structure as the structure in FIG. 3.

It is also important to have the permanent magnet material 130 extend lengthwise beyond the ends of the soft ferromagnetic poles in a flat plate embodiment such as that of FIG. 1 at 136. The permanent magnet material overhang 136 at the ends of the poles results in a preferred path for the magnetic flux that is from the pole tip 124 of each pole to the pole tips of the adjacent poles. If this overhang 136 is not present, magnetic flux would tend to go from the end of each pole to the ends of the poles on either side instead of being concentrated at the pole tips 124. This would result in lower field strength in the region of interest at the tips of each pole of the magnetic structure. In other words, the permanent magnet material overhang 136 produces a more uniform pole tip field strength along the length of the poles out to the ends of the poles.

(2) Computer Modeling

One skilled in the art would appreciate the use of three dimensional computer models to further develop and quantify the performance of these magnetic structures. A suitable computer program is used to calculate and determine what the field distributions should be, while taking into account the materials and geometry that will be employed. The AMPERES code is available from Integrated Engineering Software, AMPERES, Three-dimensional Magnetic Field Solver, (Winnipeg, Manitoba, Canada). Suitable programs, in addition to AMPERES, include, but are not limited to, TOSCA (made by Vector Fields Inc., Aurora, Ill.), ANSYS (ANSYS, Inc., Canonsburg, Pa.), POISSON, PANDIRA and POISSON SUPERFISH 2-D (Los Alamos Accelerator Code Group (LAACG), Los Alamos National Laboratory, Los Alamos, N. Mex.).

Use of this software can be used to construct and solve hybrid magnetic structure boundary element models (BEM) that incorporate all significant geometric attributes and non-linear behavior of isotropic, ferromagnetic steel, verify the fields that will be created, and mathematically evaluate the magnetic performance of the proposed model and all attributes of the fields that will be generated by the proposed model.

Those skilled in the art would appreciate that in order to perform secondary two-dimensional field calculations such as solving the field gradient problem or the force experienced by magnetized targets in the field, it is useful to start by obtaining the vector potential solution of a boundary value numerical model of the hybrid magnetic structure. After finding a numerical solution for the vector potential, then post-processing computations can be performed to find the field values and associated derived quantities.

Figure 4:
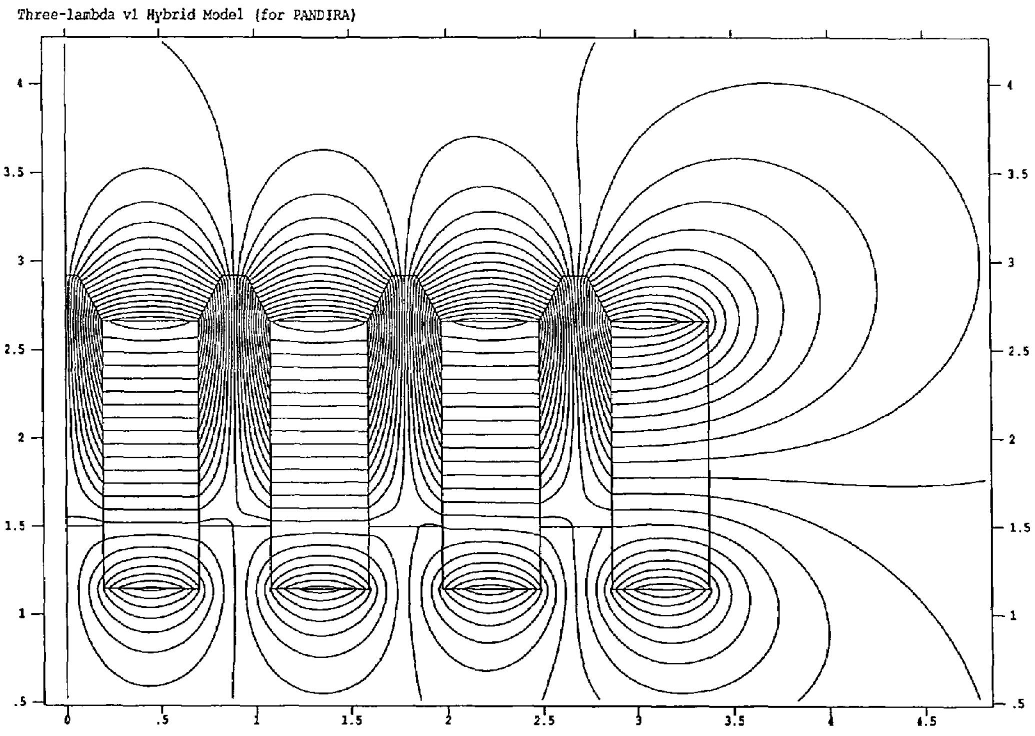
FIG. 4 is a two-dimensional modeling of the preferred hybrid magnetic structure using PANDIRA. The model shown has a geometric periodicity of 0.9 cm. Because of the left hand Dirichlet symmetry boundary, the model is a complete representation of an infinitely long structure having three full magnetic periods.

Referring now to FIG. 4, the field lines shown are lines of constant vector potential of A, where A is the vector potential of Maxwell's equations. The magnetic flux density, B, can be solved from Maxwell, B=CurlA, where CurlA is given by:

$$CurlA = \nabla \times A = \left(\frac{\partial A_z}{\partial y} - \frac{\partial A_y}{\partial z}\right)\hat{x} + \left(\frac{\partial A_x}{\partial z} - \frac{\partial A_z}{\partial x}\right)\hat{y} + \left(\frac{\partial A_x}{\partial x} - \frac{\partial A_y}{\partial y}\right)\hat{z}$$

i.e., the cross product of the partial derivatives with respect to vectors x, y and z and the 3-dimensional space vector quantity A.

The curl of A is a function which acts on the vector field A. The B field is related to the rate of change in the vector potential field A. Taken together the partial derivatives of the orthogonal components of the vector potential A yield the three components of the vector field B as given in the above expression.

An implication of this relationship between the vector potential A and the magnetic flux density B is that the proximity or density of the field lines is an indication of the relative strength of the field. Therefore, as the density of field lines in close proximity increases, the stronger the magnetic field is indicated.

The fields in the ferromagnetic poles can range from several thousand gauss at the bottom to approximately seventeen thousand gauss in the upper corners of the trapezoidal tip of the preferred embodiment. An increasing density of field lines can be seen moving from the bottom of the ferromagnetic poles to the trapezoidal pole tip area. The fields in the air outside the pole tip are correspondingly high in the region of interest for magnetic separation applications. In addition, because of the geometry and polarity of the pole tip array, high field gradients are produced in the region above the pole tips, which is central to the high performance of these magnetic structures. Thus, the force exerted on ferrimagnetic beads attached to target molecules in a typical separation process is directly proportional to the product of the B field magnitude and the gradient of the B field.

(3) Field Gradient Distributions

All magnet plates currently in use in industry have been "permanent magnet dominated" systems. This means that the field distributions of industry magnet plates are controlled by the geometry and orientations of the permanent magnets. Currently available magnet plates produce weak fields and gradients which give poor results and long separation times. The instant invention differs from the currently available magnetic separators by its use of hybrid magnets which produce significantly higher fields and gradients.

The field gradient distribution in the hybrid magnetic structure is created by the combination of permanent magnets and ferromagnetic steel poles. The gradient distributions of these hybrid structures can be controlled and shaped to produce both three-dimensional, finely structured gradients with corresponding directional forces.

When designing the hybrid magnetic structure, the shape, size and number of soft ferromagnetic poles 120 and the number of blocks of permanent magnet material 130 should be directly correlated not only to the number, shape and size of the wells or liquid containment vessels containing magnetic or magnetized material that need to be acted on, but also to the desired magnetic field levels and field gradient distributions that should be created by the hybrid magnetic structure. A main objective of any adopted dimensions is to design a particular geometry of the soft ferromagnetic poles and the blocks of permanent magnet material so that an effective amount of diffuse flux from the permanent magnet material is concentrated into the ferromagnetic poles. The desired field level and gradient in the hybrid magnetic structure is strongly correlated and directly related to the quantity and the height of the permanent magnet materials, therefore increasing the height of the ferromagnetic poles and the permanent magnet material changes the shape and strength of the field gradient. See FIG. 4 for a two dimensional view of the magnetic field created by a preferred embodiment of the hybrid magnetic structure that will act on magnetic or magnetized particles in a microtiter plate.

The gradient of the magnetic flux density B, where B is a vector quantity in three-dimensional space and from Maxwell, B=CurlA can be solved. For a vector function such as the magnetic flux density B, the gradient of B is itself a vector which points in the direction of fastest change in B. The gradient of the magnetic flux density B is given by:

$$GradB = \nabla B = \frac{\partial B}{\partial x}\hat{x} + \frac{\partial B}{\partial y}\hat{y} + \frac{\partial B}{\partial z}\hat{z}$$

i.e., the sum of the products of the partial derivatives of B with respect to x, y and z and the unit vectors $\hat{x}$, $\hat{y}$ and $\hat{z}$. The magnitude of the gradient of B is given by:

$$|\nabla B| = \left[\left(\left(\frac{\partial B}{\partial x}\right)^2 + \left(\frac{\partial B}{\partial y}\right)^2 + \left(\frac{\partial B}{\partial z}\right)^2\right)\right]^{1/2}$$

i.e., the square root of the sum of the partial derivatives of B with respect to x, y and z. The force $F_\nabla$ experienced by magnetized targets in the field, is proportional to the product, called the "force-density", of the field magnitude and the magnitude of the gradient of the field at the location of the target, i.e., $$F_\nabla \propto |B||\nabla B|.$$

C. Assembly of Hybrid Magnetic Structures

The hybrid magnetic structures are made by machining the component parts and then assembling usually by means of clamping fixtures and secured by means for holding the base, ferromagnetic pole and blocks of high field permanent magnet material together, preferably through the design of retainers and use of high strength bonding agent. A person skilled in the art would appreciate that these structures experience high-magnitude internal forces during and after assembly and require careful restraint during assembly. Because of the high field strengths of the magnetic structure's components, a system of bonding and clamping fixtures should be designed that allows for efficient and rapid fabrication of these devices. A method for assembling the preferred hybrid magnetic structure in Example 1 is described in Example 4. Also described are a system of bonding and clamping fixtures useful for assembling a hybrid magnetic structure. FIG. 6 shows part of the assembly of the hybrid magnetic structure of Example 1.

D. Instrument Adaptation of the Hybrid Magnetic Structure

The hybrid magnetic structure can be adapted for use with a number of different microtiter plates, liquid containers and a variety of commercial liquid handling robots and other instruments including 96- and 384-channel liquid handling dispensers through the design and implementation of upper interfaces and lower locator plates. The hybrid magnetic structure should be used with caution with robotic platforms having tips made from steel or other ferromagnetic material because the hybrid magnetic structure may induce a magnetic field in the tips which can result in magnetic bead loss and decreased efficiency and yields in protocols.

One way of adapting the hybrid magnetic structure is to design a machined upper interface 180 to hold the liquid container in close proximity with the hybrid magnetic structure. The machine upper interface can be simply a bracket or adaptor for holding a microtiter plate in place with the magnetic structure. Various applications for which a separate interface would be necessary would be for applications involving a number of different types of microtiter plates, different protocols, different manual or robotic steps in these protocols and for use with various liquid handling robots and apparatuses. Several interfaces have been designed and used in conjunction with the hybrid magnetic structure. They are specialized for different applications and thus are made to be removable and interchangeable.

Large-scale processes and experiments are typically built around robots which usually have one or more robotic arms which move microtiter plates and other types of containment vessels from platform to platform or which have heads equipped with multiple syringes or other fluid handling mechanisms. To facilitate platform differences, a lower locator plate 190 can be designed to insure that the hybrid magnetic structure and any liquid containers seated above it are positioned correctly on the horizontal plane to prevent damage due to misalignment to the syringes or other fluid handling mechanisms.

In a preferred embodiment, a removable microtiter plate interface can be attached to the top of the hybrid magnetic plates.

E. Variations for Specialized Function

The shape and size of the soft ferromagnetic poles 120 and the permanent magnet material 130 influences where the desired field concentration is located. Ferromagnetic poles and the permanent magnet material of different shapes and sizes can be easily ordered from industry vendors. Therefore it is possible to make variations of the hybrid magnetic structure by varying aspects of the hybrid magnetic structure to change the field distribution for specialized applications. The ferromagnetic poles and blocks of permanent magnet materials can be machined to a specialized shape to produce the desired field gradient.

When viewed three-dimensionally, the ferromagnetic poles 120 (not including the tip section) and blocks of permanent magnet materials 130 can be machined to be of a general shape, with examples of preferred shapes including, but not limited to, annular or partially annular, cylindrical, toroidal, helical, conical, T-shaped, inverted L-shaped, a triangular prism, a quadrangular prism, a hexagonal prism or any other multi-sided polyhedron.

The ferromagnetic poles 120 and blocks of permanent magnet materials 130 have a cross-sectional area. Examples of preferred cross-sectional shapes include but are not limited to, square, rectangle, circle, elliptical, wedge, triangle, quadrilateral, and other polygons.

The pole tip 124 can be of any desired shape, wherein a cross-sectional view of a preferred pole tip shape includes but is not limited to, trapezoid, T-shaped, inverted L-shaped, circle, triangle, elliptical, conical, polyhedrons such as, square, rectangle, trapezium, rhombus, rhomboid, or any other shape depending on the desired magnetic field and gradient to be produced.

Figure 10A:
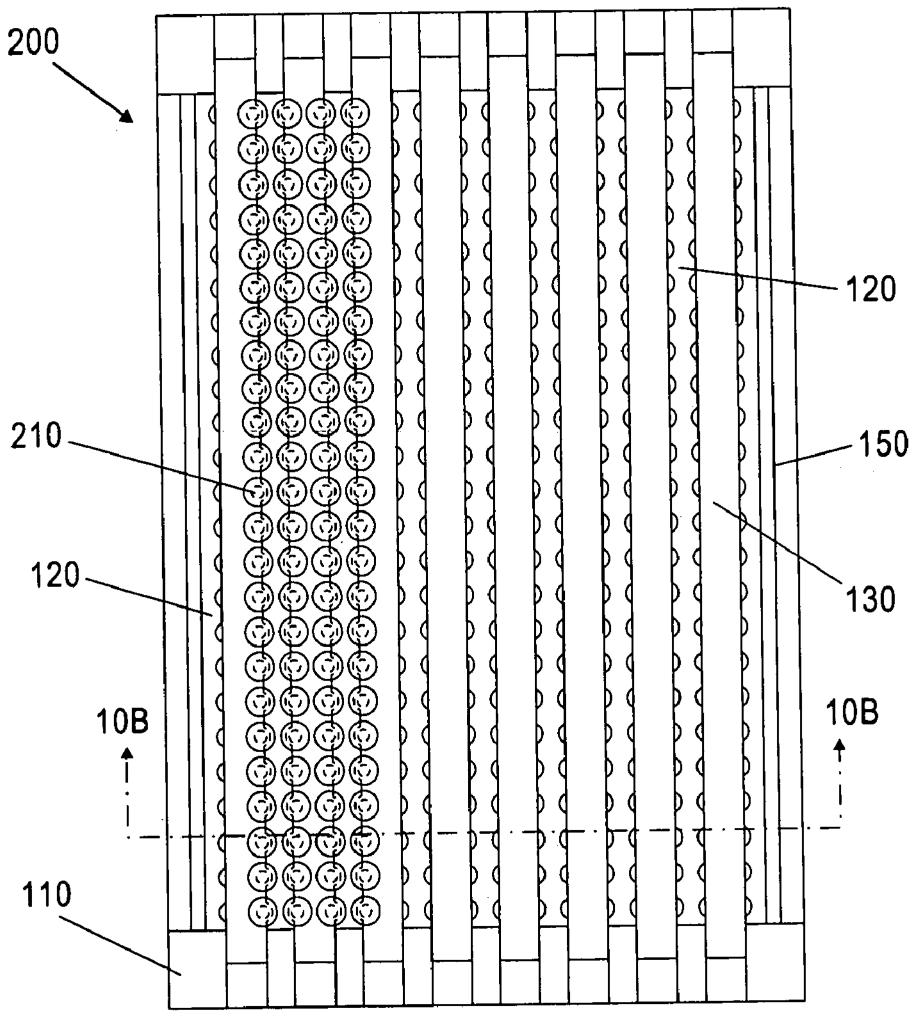
FIG. 10 is a top view (FIG. 10A) and cross-sectional view (FIG. 10B) of a hybrid magnetic structure 200 with T-shaped ferromagnetic poles having circular cut-outs for microtiter plate wells with two rows of microtiter wells from a 384-well microtiter plate.
Figure 10B:
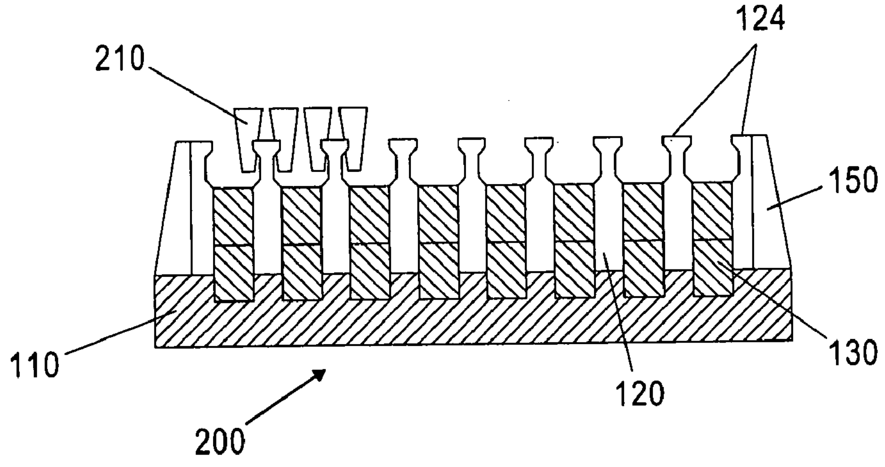

In one embodiment, the length of the pole has shaped cut-outs 128 for close contact with microplate wells, resulting in a pole having a cross-section that is T-shaped at the widest portions of the tip. In Example 9, FIGS. 10A and 10B show a hybrid magnetic structure 200 having T-shaped ferromagnetic poles that create gradients near the upper part of the T-shape, whereas trapezoidal-shaped tips 124 of ferromagnetic poles (FIG. 1) create field gradients as shown in FIG. 4. The gradients near the upper part of the T-shape, can allow, for example, magnetized particles to be strongly held high up in microtiter plate wells for effective separation and extraction of the magnetized particles from the solution, while the trapezoidal-shaped pole tips 124 concentrate magnetized particles in or near the bottom tip of conical-shaped microtiter plate wells. In a preferred embodiment, the well cutouts 128 should contour the shape and size of the well or container to be acted on to maintain close contact between the pole 120 and the container.

It is contemplated that the shape of the pole tip 124 can further be designed to address the shape of the container or containment vessel to be acted on. In one aspect, the improvement comprising, the shape of the pole tip 124 is asymmetrical as shown in the cross-section of the tip in FIG. 12B.4 in order to create unique field gradients that concentrate flux asymmetrically on one side of the pole tip. The gradients created at the widest portion of the tip can allow, for example, magnetized particles to be strongly held in one concentrated area on one side of the microtiter plate wells for effective separation and extraction of the magnetized particles from the solution.

Figure 12A:
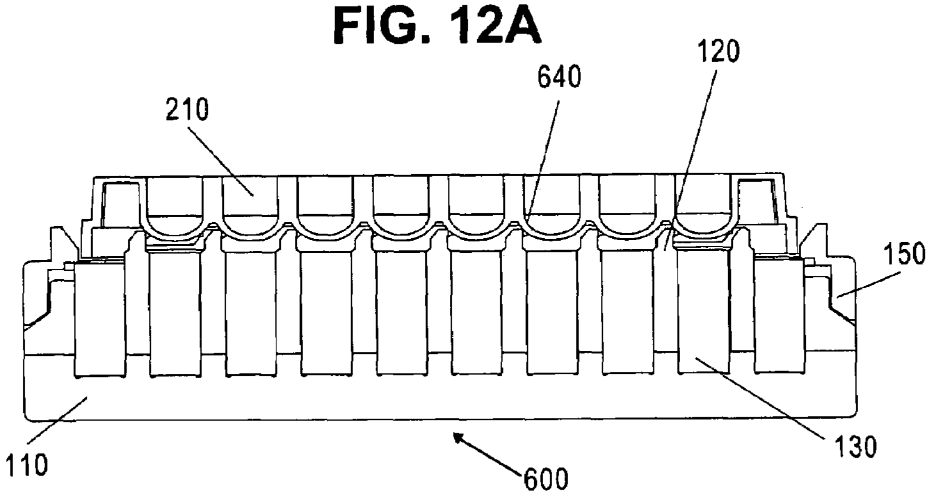
FIG. 12A is a cross-sectional view of a hybrid magnetic structure.
Figure 12B:
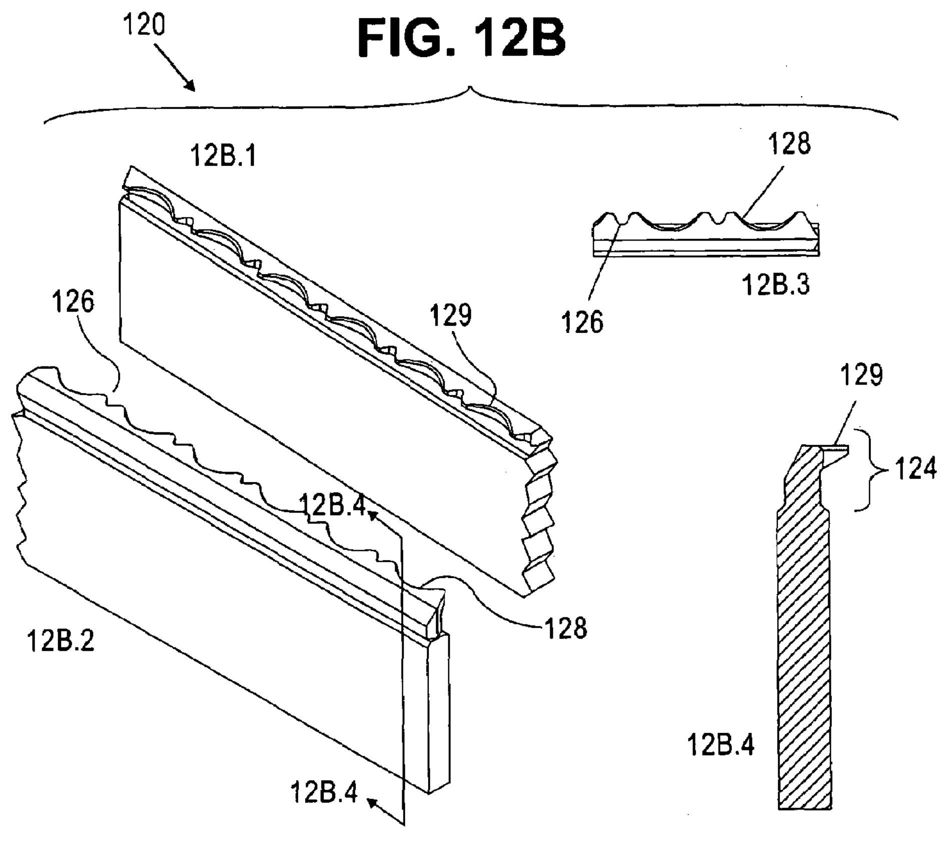
FIG. 12B is multiple views of an asymmetric ferromagnetic pole.

In another aspect, the improvement further comprising the ferromagnetic pole 120 features notches 126 between well cut-outs 128 to increase the field strength that liquid containers (e.g., microplate wells) are exposed to from the hybrid structure. FIG. 12B shows an example wherein at various points along the pole length 120, notches 126 can be made to increase field strength of the hybrid magnetic structure. In a preferred embodiment, the notches 126 approach but do not pass the center line of the pole 120. The size and shape of the notches depend upon the size and shape of the wells of the liquid containers to be acted on, and the desired field distribution. For example, it is contemplated that in an embodiment for microtiter plates using conical wells, that the pole 120 feature small cutouts for smaller wells and large rounded notches for increasing field strength. Similarly, shown in FIG. 12, smaller notches 126 are made in the poles 120 for providing increased field strength within the wells.

Referring now to FIG. 12B, the ability of the tip 124 to contour the shape of the liquid container and increase field levels is improved by a chamfer 129, i.e., angled surface, to allow the liquid container to come into close proximity or contact with the hybrid magnetic structure. The chamfer 129 may be of any applicable size or width, thus allowing the pole to contour the shape of the liquid container(s) as desired. The chamfer 129 may also serve to seat the liquid container securely to the hybrid magnetic structure, to smooth any sharp edges for safety, or to seat an upper interface or attachment used to securely seat any multi-well container onto the hybrid magnetic structure. The chamfer 129 allows the structure to transmit an increased amount of magnetic flux into the lower recesses of a well 640 of a microtiter plate.

In a specific embodiment, the chamfer 129 allows additional conformance of the pole tip 124 to the bottom 640 of a round-bottom microtiter plate well to hold down magnetized particles tightly at the bottom of the sides of the well and distribute it in a beneficial way. Even or specialized distribution of particles and high fields to hold the particles down tightly is useful, for example, in the wash and aspiration steps of particle separation processes. If the magnetized particles are evenly distributed along the bottom sides of the well and held tightly, this prevents aspiration and mixing of the magnetized particles and thereby prevents particle loss during these steps.

Figure 15:
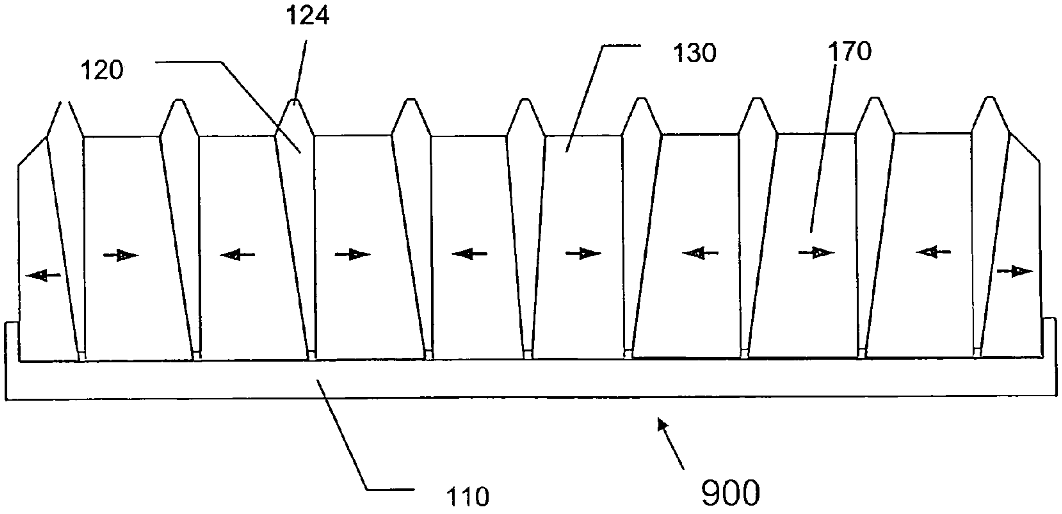
FIG. 15 shows a compact hybrid magnetic structure having non-uniform wedge shaped poles and blocks of permanent magnet material.

It is also contemplated to make hybrid magnetic structures wherein the pole tip shapes vary from one pole to another to create unique field gradients. Referring to FIG. 15, the ferromagnetic poles can be non-uniform wedge-shaped poles to create compactness in the hybrid magnetic structure and for tuning of the field distribution for periodic and non-periodic effects. This compact structure may find use in applications needing a hybrid magnetic structure with a smaller footprint without compromising the need for high fields and specialized field distributions.

Permanent magnet materials of different shapes and sizes can be easily ordered from industry vendors and are available commercially in various shapes and sizes. Therefore, the blocks of permanent magnet material 130 can be made up of smaller blocks of permanent magnet material that, when put together, conform to the desired dimension. Smaller blocks of permanent magnet material may be cheaper and easier to work with. Their use does not affect the field strength generated by the hybrid magnetic structure, meaning that a single block of permanent magnet material is not necessarily more preferred than several blocks of permanent magnets which put together conform to the same desired dimensions. See Example 1 for an example in which multiple blocks of permanent magnet materials was used.

Figure 11A:
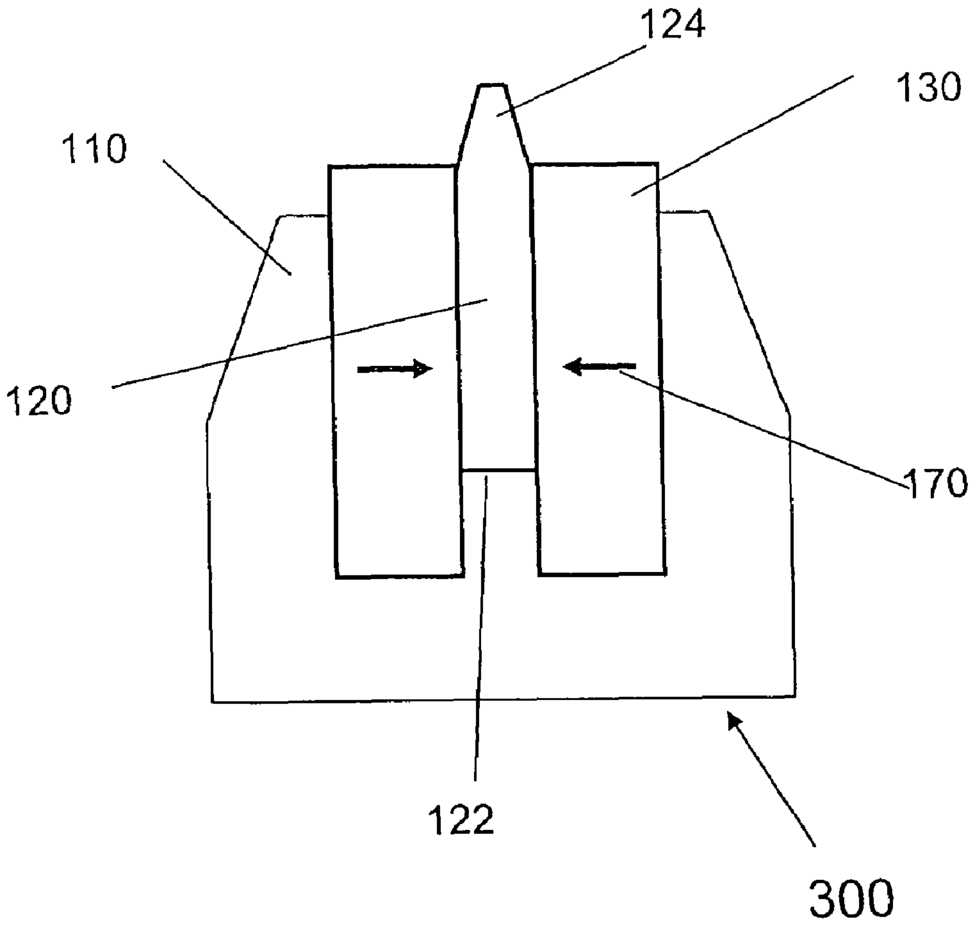
FIG. 11A is a side view of a single pole hybrid magnetic structure.

Referring now to FIG. 11, other variations contemplated include a hybrid magnetic structure 300 having a single pole configuration with permanent magnet material 130 to the left and right of the single ferromagnetic pole 120 as shown in FIG. 11A. This configuration would produce a high performance single-pole hybrid magnetic structure and may be scaled to produce approximately 1 Tesla field at the pole tip, and fields of 190 Gauss up to 2 cm above the tip.

Alternatively hybrid magnetic structures can be designed so that the ferromagnetic poles 120 are radially arranged to produce strong gradient distributions around cylindrical or conical vessels for target separation in either static or flow separation applications such as the embodiment 400 in FIG. 1B. In this embodiment 400, the ferromagnetic poles 120 and blocks of permanent magnet material 130 are wedge-shaped, thus accommodating the radial hybrid magnetic structure. This creates a magnetic periodic field in the center of the radially arranged ferromagnetic poles 120 and permanent magnet material 130, flowing from each pole tip to the adjacent pole tip around the center.

These variations demonstrate that the ferromagnetic poles and the blocks of permanent magnet material can be machined to various sizes and shapes depending on the application.

As shown in the hybrid magnetic structure 400, lower blocks of permanent magnet material 270 can be assembled under the bottom edge of the ferromagnetic pole 120 to increase performance of the hybrid magnetic structure. Notice that for the magnetic circuit to be most efficient, the magnetization orientations 170 of all blocks of permanent magnet material around each pole piece 120 must be uniformly facing either out of or into the pole. Therefore, the magnetization orientation 170 of each lower block of permanent magnet material 270 under each pole 120 should be axially facing either toward or away from the pole, in the opposite direction of the magnetization orientation 170 of the next adjacent lower block of permanent magnet material 270 under a pole.

In another aspect, these lower blocks of permanent magnet material 270 can act as field adjustment elements and can be selectively added to the assembly below specific poles to improve and increase or decrease the field levels of a specific pole. The improvement comprising these field adjustment elements can increase or decrease field levels at about 1 cm above a selected pole tip by 0-15% or more depending on their dimensions and orientations relative to the other permanent magnets around the selected pole.

Figure 11B:
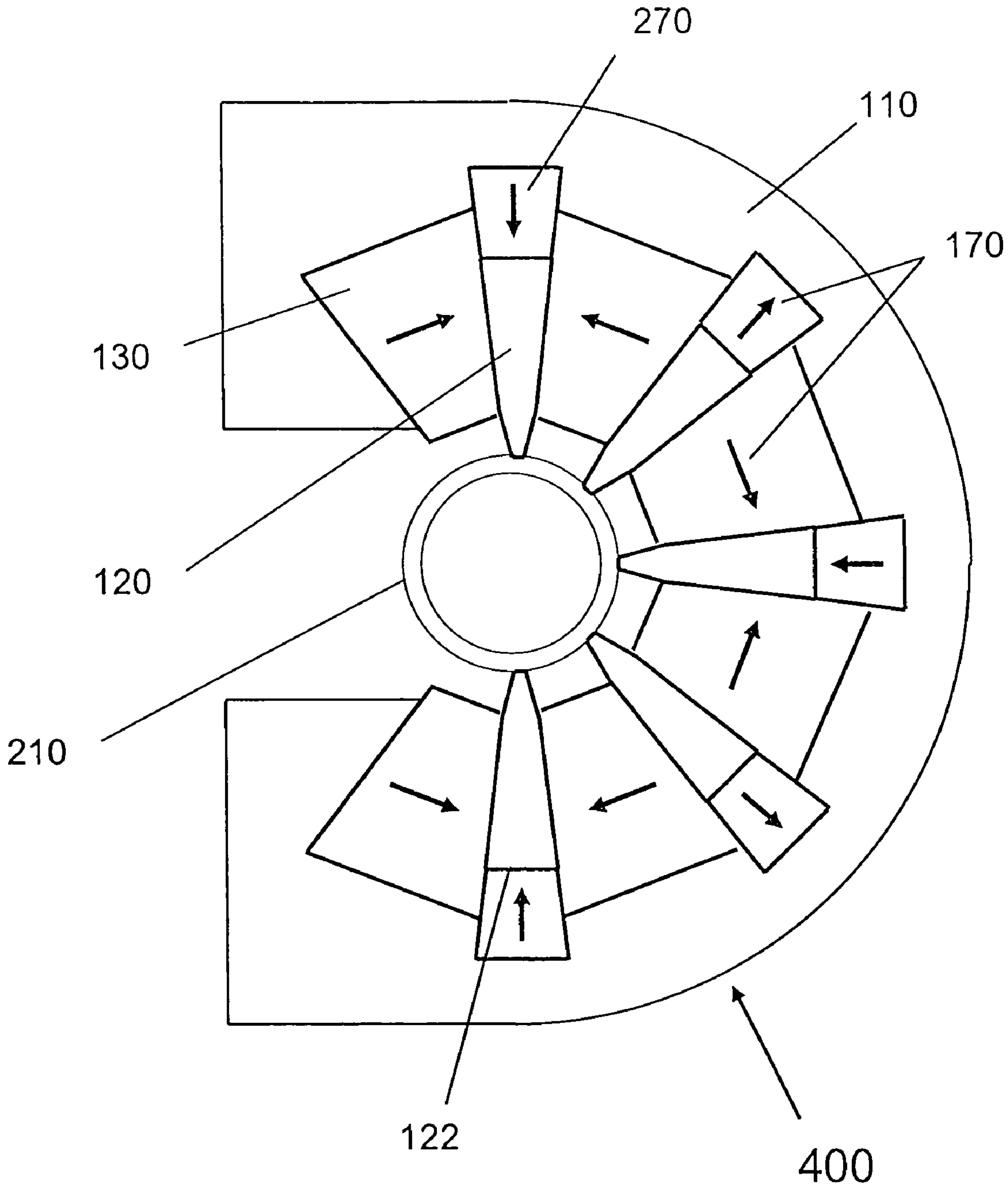
FIG. 11B is a top view of a hybrid magnetic structure having radially arranged wedge-shaped ferromagnetic poles and blocks of permanent magnet material.
Figure 11C:
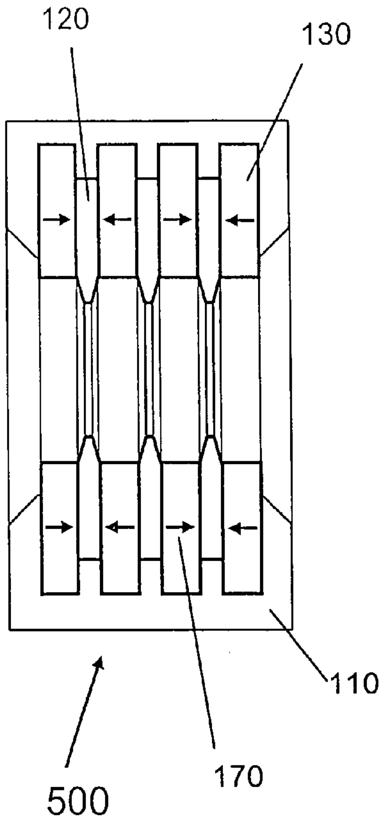
FIG. 11C is a cross-sectional view of an annular hybrid magnetic structure.
Figure 11D:
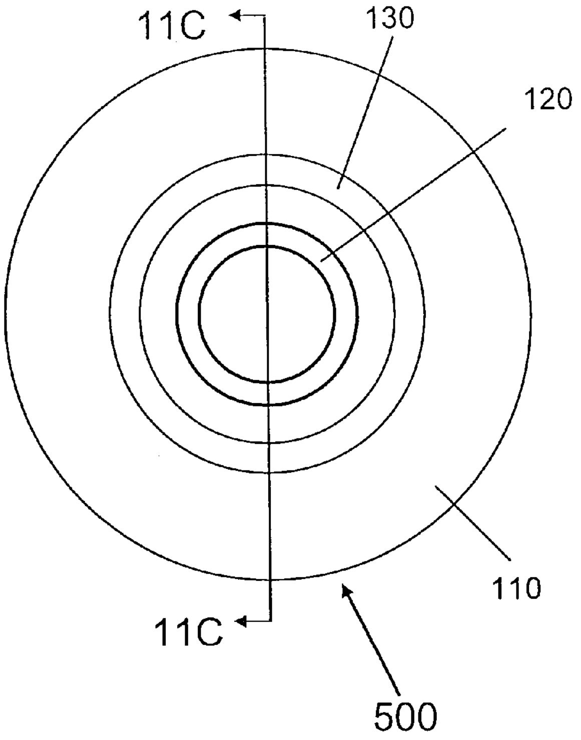
FIG. 11D is an end view of an annular hybrid magnetic structure.

Referring to FIGS. 11C and 11D, hybrid magnetic structures can also be made annularly or partially annular for application to liquid containment vessels, flow channels or other target objects. In one such embodiment of the hybrid magnetic structure 500, the annular ferromagnetic pole 120 is "sandwiched" between permanent magnet materials 130 that are also shaped annularly, with the magnetization orientation 170 of each block of permanent magnet material in the opposite direction of each adjacent permanent magnet material and parallel to the axis of rotation of the annular pole 120. Because the ferromagnetic poles 120 and permanent magnet material 130 are annular or partially annular, stacking would be permitted. An annular base 110 holds the poles 120 and permanent magnet material 130. This embodiment would create strong fields within the center of the stacked rings of ferromagnetic poles and permanent magnet material, with the magnetic periodicity flowing laterally down through the center of the hybrid magnet structure.

These two contemplated variations of the hybrid magnet structure demonstrate that the ferromagnetic poles 120 and permanent magnet materials 130 can be shaped annular or partially annular, cylindrical, toroidal, helical, T-shaped, inverted L-shaped, a triangular prism, a quadrangular prism, a hexagonal prism or any other polyhedron, wherein a cross-sectional area of the shape include but is not limited to, square, rectangle, circle, elliptical, wedge, triangle, quadrilateral, and other polygons. Alternatively, the ferromagnetic poles 120 and permanent magnet materials 130 can be arranged and assembled to form hybrid magnetic structures having the above shapes, depending upon the type of magnetic field sought to be created, the desired application and commercial or application constraints.

Furthermore, the geometric periodicity, which can be interpreted also as the distance or length over which the geometric pattern of ferromagnetic poles 120 and blocks of permanent magnet material 130 is repeated in periodic array, can be arbitrary in the sense that it can be varied according to these same constraints. In a preferred embodiment, the magnetic period length is 18 mm, therefore making the geometric periodicity 9 mm. Arbitrary periodicity variants can be made with period lengths other than 18 and 9 mm such as the embodiments shown in FIG. 11. It is also contemplated that some variants may have periods that vary as a function of a given variable, X, where X is the direction orthogonal and perpendicular to a lateral plane of the poles.

Figure 13A:
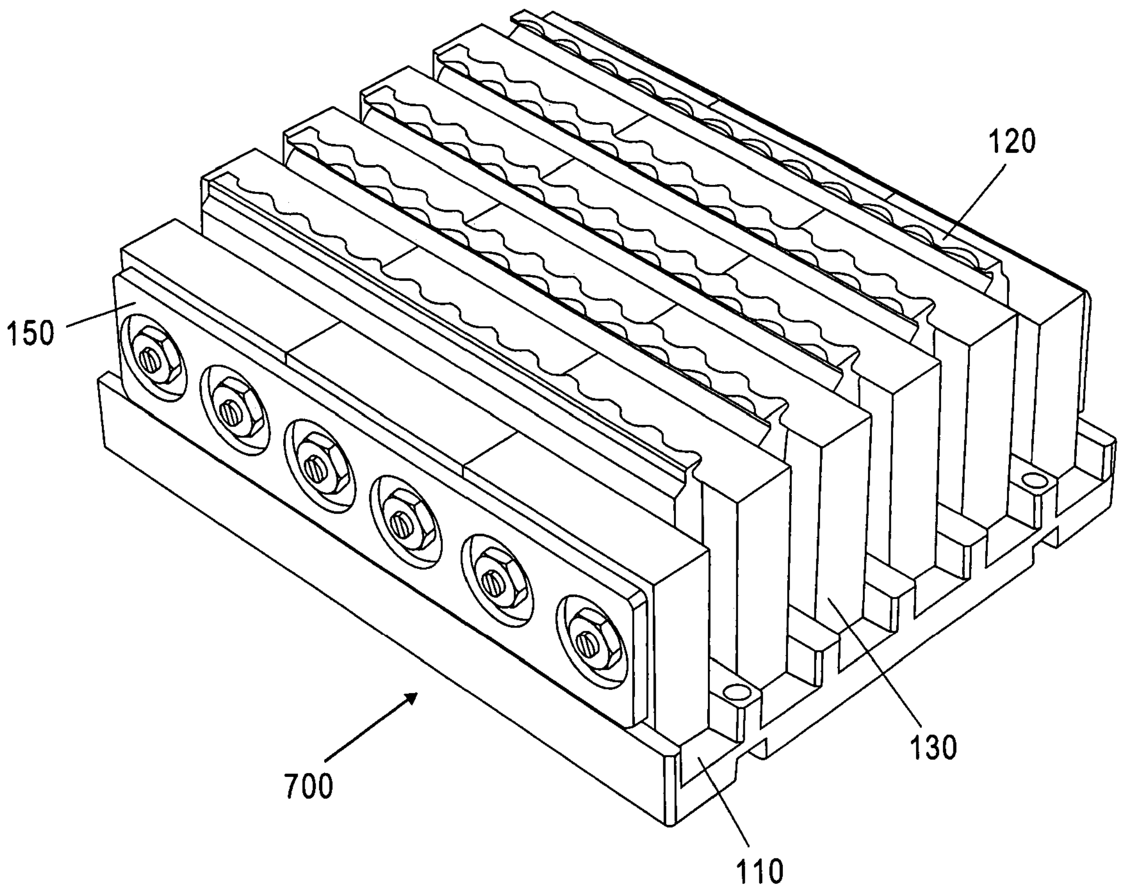
FIG. 13A is a perspective view of the assembled long period hybrid magnetic structure.
Figure 13B:
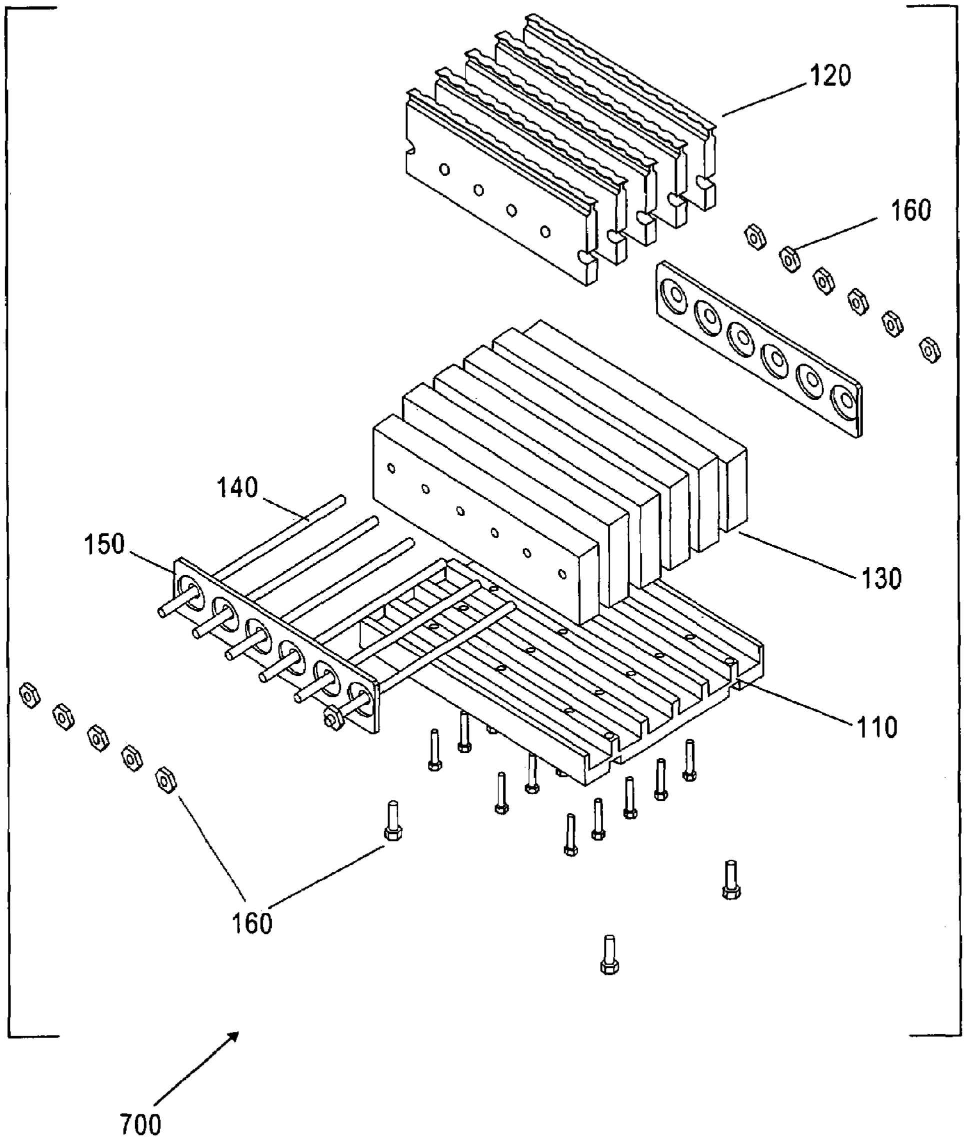
FIG. 13B is an exploded view of the long period hybrid magnetic structure.

In another aspect, where the period is lengthened and the structure is scaled up in size, the assembled hybrid magnetic structure will experience large internal forces. Referring now to FIG. 13, retainer rods 140 that run through a long period hybrid magnetic structure 700 can be made to secure the structure together. These retainer rods 140 are preferably made of non-magnetic materials as the retainers 150 and are preferably round so as to cause the least disruption in the flow of flux through the structure (FIG. 13B). In a preferred embodiment, the retainer rods pass through the hybrid magnetic structure at the unsaturated portions of the poles having less flux.

F. Applications

These hybrid magnetic structures represent an enabling device to advance modern, high-throughput, production sequencing capabilities and to improve general bio-assay techniques. Their performance significantly exceeds that of currently available commercial magnet plates. In addition, the use of easy-to-machine, soft ferromagnetic poles allows for significant flexibility of design and application of these devices. Examples of their adaptation to a range of experimental and production instruments are described herein in the Examples section.

The hybrid magnetic structure can be designed to act directionally on magnetized particles by creating a fine structure of field gradients which can be made to match the structure of liquid containers, containment vessels and various microtiter plate well arrays. They are not restricted to use with microtiter plates and can be used in conjunction with other liquid container types as well, for example, flat trays, unpartitioned containers, round bottom test tubes and conical centrifuge tubes.

One application that the invention can be used for is separation of particles from a solution. For example, the hybrid magnetic structure can be used to separate magnetized DNA fragments from bacterial cellular matter after plasmid DNA amplification and to separate ferrite particles from DNA that has released those particles after processing. Separation time depends on the viscosity and other characteristics of the solution that the particle is suspended in. In another application, the hybrid magnetic structure may be separating and holding detached magnetic beads from specific particles. This type of separation can occur in a small fraction of a second. Magnetized particles in a highly viscous, deep solution may require more than a minute.

An example of a common and standard method of using hybrid magnetic structures for an application involving separation of particles from a solution is DNA clean-up and separation. The basic method used with currently available magnet plates is suitable for use with DNA, RNA, proteins and other cellular particles on the present hybrid magnetic structure.

Large-scale processes are typically built around robots which usually have one or more robotic arms which move microtiter plates and other types of liquid holders from platform to platform or which have heads equipped with multiple syringes or other fluid handling mechanisms. The hybrid magnetic structure can be adapted, through the design and implementation of upper interfaces and lower locator plates as described in the earlier section describing instrument adaptation of the hybrid magnetic structure, for use in large-scale, high throughput processes which may involve a number of different microtiter plates, liquid containers and a variety of commercial liquid handling robots and other instruments including 96- and 384-channel liquid handling dispensers.

Various applications for which a separate interface would be necessary would be for applications involving a number of different types of microtiter plates, different protocols, different manual or robotic steps in these protocols and for use with various liquid handling robots and apparatuses. To facilitate platform differences, a lower locator plate can be designed to insure that the hybrid magnetic structure and any liquid containers seated above it are positioned correctly on the X-Y axis to prevent damage to the syringes or other fluid handling mechanisms due to misalignment.

Several interfaces have been designed and used in conjunction with the hybrid magnetic structure. They are specialized for different applications and thus are made to be removable and interchangeable.

In applications involving containment vessels such as microtiter plates 210, the wells of the microtiter plate are typically touching or in very close proximity to the hybrid magnetic structure. By "close proximity" it is meant that the containment vessel should most preferably be at or within 1-2 mm of the pole tips 124 of the hybrid magnetic structure surface. See FIG. 9 which shows the wells of a microtiter plate 210 in relation to a preferred embodiment of the hybrid magnetic structure 100. Because the field gradient decays rapidly outside of 1 mm, as shown by the example in FIG. 9, the wells 210 preferably should be within at least 2 mm of the surface of the ferromagnetic pole tips 124 of the hybrid magnetic structure.

Loading of the microtiter plate wells is done by various instruments ranging from hand pipettors to large liquid handling robots with arrays of syringe-like devices. The hybrid magnetic plates are adaptable for use on a variety of these liquid handling systems also by creating specialized interfaces. Measurement of the separation is accomplished by means of visual inspection, photospectrometric devices or other analytic means such as monitoring of down-stream sequencing results in the specific case of DNA sequencing applications.

The hybrid magnetic structure can further comprise a magnetically attachable protective cover to prevent unwanted interaction with another hybrid magnetic structure and to provide a surface for warning against bodily injury. For example, a warning label can be adhered to the cover to warn users to keep pacemakers back by at least 1 foot; if more than one structure is being used, to keep the hybrid magnetic structures separated from each other; and a user should not hold more than one structure at once.

EXAMPLE 1

Hybrid Magnetic Structure for Use with 96- and 384-Well Microtiter Plates

Referring now to FIGS. 1 and 2, shown is a preferred embodiment of the hybrid magnetic structure for applications involving 96- or 384-well microtiter plates. FIGS. 1 and 2 show the design adopted for the preferred core assembly 100. The machined base plate 110, which was fashioned from aluminum and then clear anodized, was made 5.3 inches×3.64 inches wide×0.375 inches tall to permit a standard microtiter plate to be seated comfortably atop the hybrid magnet structure. The base 110 has 9 slots or grooves 112 to allow a block or blocks of permanent magnet material 130 to sit in each slot. The eight soft ferromagnetic poles 120 sit on the raised spacings between the slots 112. One long notch was created on one long side of the base 110. Two smaller notches were made, one at each end of the opposite long side. This was done to create an asymmetric base plate with a front side and a back side, which later aids in orienting the hybrid magnetic plate correctly with the microtiter plate and any robotic equipment. Each side of the base 110 contains two holes of an effective diameter for fasteners to fit through. The fasteners 160 (shown in FIG. 2) hold the retainers 150 to the upper surface of the base 110 at the sides of the base 110.

Two distinct magnet retainers 150 were made in order to accommodate the different shaped sides of the base plate because the front side and the back side were notched differently. Both retainers 150 were pyramid shaped and fitted snugly to the blocks of permanent magnet material 130 adjacent to the retainers. See the exploded view in FIG. 2 which shows the correct orientation of the retainers in relation to the base plate and blocks of permanent magnet material.

It was determined through field modeling that the blocks of permanent magnet material 120 should be approximately 4.55 inches in length and fitted to the grooves. A single block of permanent magnet material of the correct dimensions may be used in each slot 112. However, because blocks of commercially available permanent magnet material (Nd—Fe—B magnets) 130, that are 0.2"×0.295"×1.875" and easily obtained, these blocks were used. When stacked atop each other, the blocks are the desired height of about 0.6". As shown in the exploded view of FIG. 2, each row contains four 1.875" length magnets and two 0.80" magnets, which are machined from a single 1.875" long block magnet.

Now referring to FIG. 3, the blocks of permanent magnet material 130 were assembled onto the base, making sure that the magnetization orientations 170 of the permanent magnet material were oriented in the opposite direction of each adjacent block of permanent magnet material.

The soft ferromagnetic poles 120 were machined from soft steel: 1010, 1006 or 1020 hot rolled. The machine shop was instructed to minimize heat during machining, maintain the tolerances to +/−0.002, and finish the poles to 63 RMS. The steel pole pieces were about 4.26 inches long, 0.15 inches wide and 0.55 inches in height. The tips of the steel poles 124 were trapezoidal in shape, with the angle of the tips at 26° on each side and 0.1 inches in height.

Figure 9:
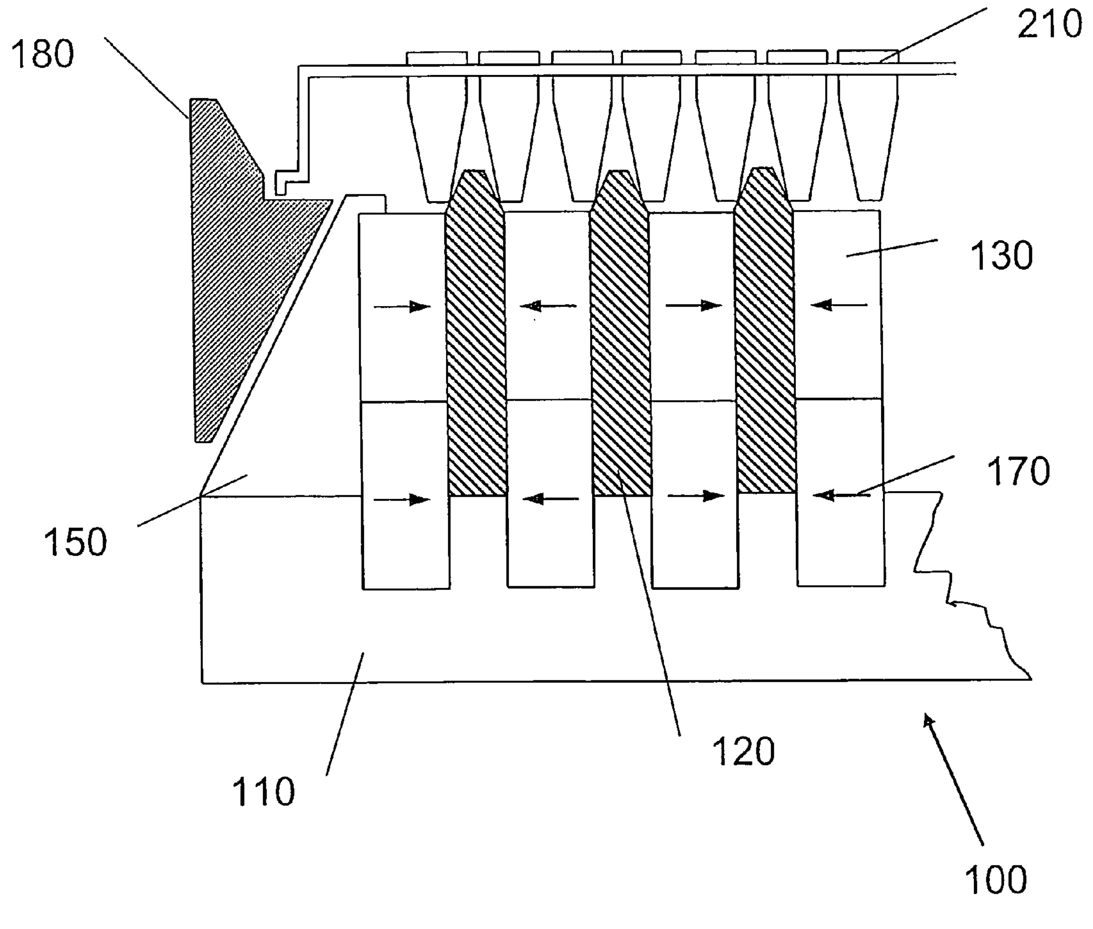
FIG. 9 is a cross-section of the preferred hybrid magnetic structure shown with conical microtiter wells to demonstrate how the wells interface with the structure in a preferred embodiment.

Eight poles was determined to be the desired number of poles to create the desired shape of the field gradient necessary for this application to act on the magnetized particles in a 384-well microtiter plate. When used with a 384-well microtiter plate, each pole is straddled by 2 rows of wells on each side. Nine poles was determined to be the desired number of poles to create the desired shape of the field gradient necessary for this hybrid magnetic structure to act on the magnetized particles in a 96-well microtiter plate. When used with a 96-well microtiter plate, each row of wells is located between 2 poles of the magnetic structure. If the microtiter plate is a flat-bottom plate, the plate sits directly on the steel pole tips. If the wells of the microtiter plate are conical in shape, the wells sit on the hybrid magnetic structure as shown in FIG. 9.

EXAMPLE 2

2-D Modeling of Magnetic Structures

Referring now to FIG. 4, two and three dimensional computer models were constructed to further develop and quantify performance of one embodiment of the hybrid magnetic structure. The field plot shown in FIG. 4 is a 2-D boundary value model solved by the code PANDIRA which is a member of the POISSON SUPERFISH codes. The axes of FIG. 4 are in centimeters. The left side of the model is a Dirichlet boundary and implies mirror image symmetry. The model shown has a geometric periodicity of 0.9 cm which is the distance from the center of one pole to the center of the next pole. The magnetic periodicity is twice that or 1.8 cm. Because of the left hand Dirichlet symmetry boundary, the model is a complete representation of an infinitely long structure having three full magnetic periods. The open boundaries at the right of the structure allow complete modeling of the truncation or end-effect fields.

The field lines shown are lines of constant vector potential A. Since, from Maxwell, B=CurlA where B is the magnetic flux density, the proximity or density of the field lines is an indication of the relative strength of the field. An increasing density of field lines can be seen moving from the bottom of the soft ferromagnetic poles to the trapezoidal pole tip area.

The high field gradients produced in the region above the pole tips are central to the high performance of this embodiment of the hybrid magnetic structure. It is within this region wherein the wells of microtiter plates containing ferromagnetic beads and the solution to be manipulated will be placed and acted upon by the high field gradients. The force exerted on the ferrimagnetic beads attached to target molecules in a typical separation process will be directly proportional to the product of the B field magnitude and the gradient of the B field. The fields in the pole range from several thousand gauss at the bottom to approximately seventeen thousand gauss in the upper corners of the trapezoidal tip. The fields in the air outside the pole tip are correspondingly high in the region of interest for magnetic separation applications. In addition, because of the geometry and polarity of the pole tip array, high field gradients are produced in the region above the trapezoidal pole tips.

EXAMPLE 3

Field Strength Comparison Test

Referring now to FIG. 5, the fields of the high performance hybrid magnetic structure of Example 1 are both stronger and extend farther than those of any commercial magnetic plates tested. The invention produces fields and gradients that are up to four times greater than previous industry-standard magnet plates and a more beneficial field distribution for a number of important applications.

Figure 5A:
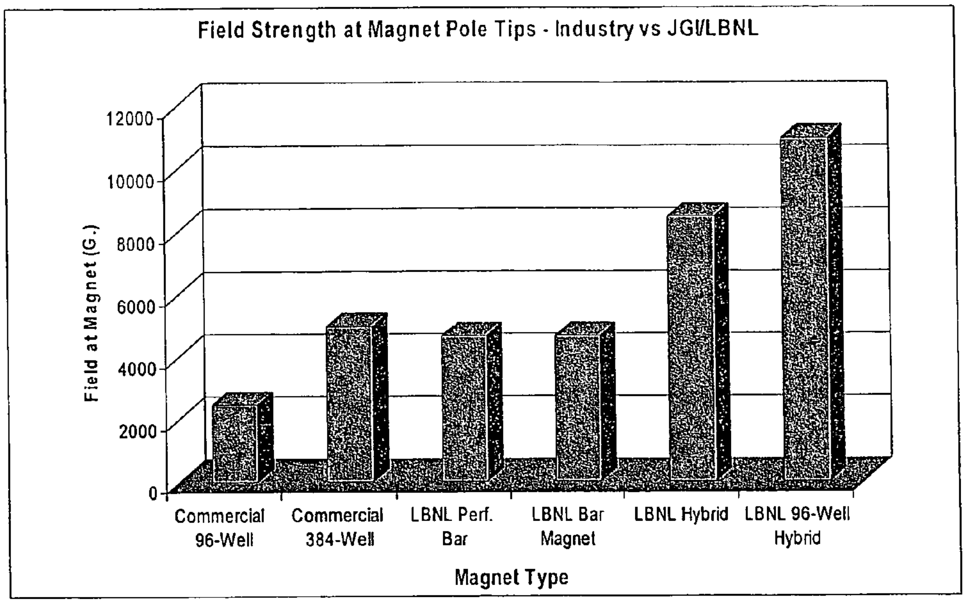
FIG. 5A is a field strength comparison of six magnet structures at the hybrid magnetic surface.
Figure 5B:
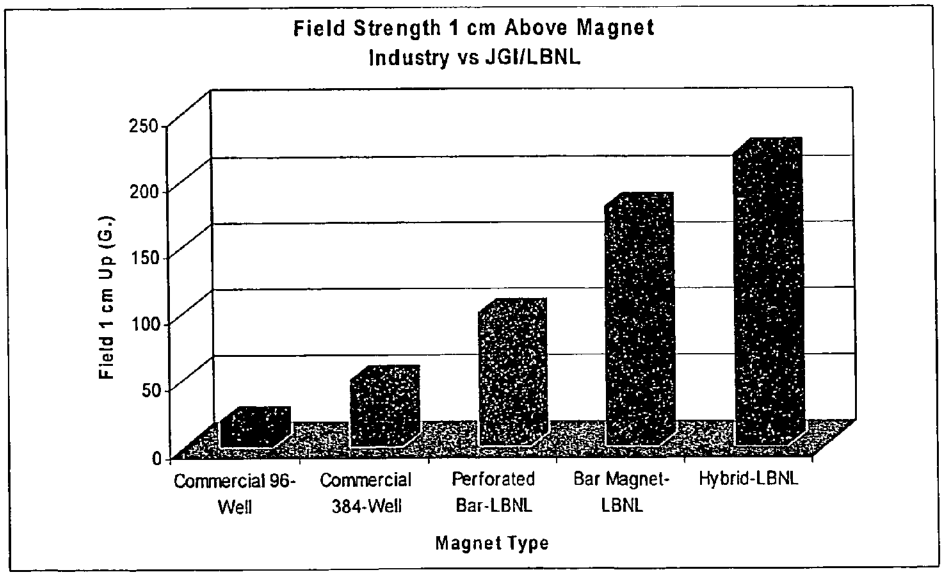
FIG. 5B is a field strength comparison of five magnet structures at 1 cm away from the surface. The magnet structures tested were: a commercial well magnet, commercial 384-well magnet, perforated magnet, bar magnet, a 384-well hybrid magnetic structure and a 96-well hybrid magnetic structure.

Relative field strengths of five or six different magnet structures are given in FIGS. 5A and 5B. Four of the magnet structures (with "LBL" designation) were developed at Joint Genome Institute/Lawrence Berkeley National Laboratory. The other two are currently available commercially magnet plates. The field strength was measured at two heights, close (less than 0.5 mm) to the magnet structure surface (FIG. 5A) and at 1 cm above the magnet structure surface (FIG. 5B). Measurements were made using a commercially available Hall effect probe. The strength of the magnetic field at the magnet surface and 1 cm above were measured in Gauss (G). The present hybrid magnetic structure demonstrates field strengths that are 225 G at 1 cm above the magnet and at 8,500 G at the magnet's surface.

As can be seen from the graph in FIG. 5, the hybrid magnetic structure produces fields that are 80% greater than the PROLINX-384 (PROLINX, Inc., Bothell, Wash.) magnet plate, which is the best performing of the industry magnet plates tested. More importantly, the fields at a distance of 1 cm above the hybrid magnetic structure are more than 300% stronger than those of the commercial magnet plates. This implies that the field decay above the hybrid magnet structure is significantly more gradual than that of available commercial magnet plates. This aspect of the hybrid magnetic structure allows it to exert much stronger forces on magnetized entities that are higher above the magnetic structure, e.g., magnetized DNA or other molecular particles that are in the upper reaches of microtiter plate wells.

When compared to the Atlantic Industrial Models "donut plate", which is perhaps the most commonly used commercial magnet plate, the performance differential is more dramatic. The maximum fields of the hybrid magnetic structure are approximately 900% greater while the fields at 1 cm are again more than 300% stronger.

The higher maximum fields of the hybrid magnetic structure result in greater holding forces on magnetized entities that are being processed as well as faster draw-down. Some variations of these hybrid magnetic structures have exhibited maximum fields in excess of 9000.0 G. The design of these structures is easily scalable to allow for field increases to significantly above 1.0 Tesla (10000.0 G).

EXAMPLE 4

Assembling the Hybrid Magnetic Structure

The component parts are bonded into a monolithic structure using unfilled epoxy with a minimum cured strength of 2500 psi and working time of approximately thirty minutes. A typical cure time for this type of epoxy will be approximately 8 hours. This magnetic structure includes high strength, rare-earth permanent magnets and ferromagnetic material. The interactive forces between these components are strong and increase in strength as the stages of assembly progress. Caution should be exercised at all time and appropriate safety equipment should be used during assembly. Permanent magnets are brittle and can fragment on impact. Safety glasses should be worn at all times during assembly.

The component parts of the hybrid magnetic structure of Example 1 are shown in FIG. 1 and in the exploded view in FIG. 2. The component parts necessary for this embodiment of the hybrid magnetic structure are the magnet base 110, ferromagnetic poles 120, permanent magnet blocks 130, magnet retainers 150 and fastener means 160 of securing the base 110 and the retainers 150.

This Example describes a method of assembling a hybrid magnetic structure that has 9 ferromagnetic poles by means of bonding fixtures to aid in assembly. Referring to FIG. 6, the bonding fixtures, as used in this method of assembly, are: bonding fixture base 230, end stop 240, pusher bar, lower magnet clamp, pole alignment clamp 250, upper magnet clamp, magnet side clamp and screws 260 used to secure the bonding fixtures. FIG. 6 shows the bonding fixture base 230, end stop 240 and the pole alignment clamp 250 to illustrate the kinds of fixtures that can be devised.

The magnet clamps used in this Example possess the same general shape and purpose as the pole alignment clamp shown in FIG. 6. The main difference between the pole alignment clamp 250 and the magnet clamps is that the magnet clamps have series of holes over each magnet slot so screws can be screwed in to hold the permanent magnet blocks or retainers in place during the curing process.

The pole alignment clamp 250 was made to be the same length as the ferromagnetic poles. The magnet clamps in general were made to be the same length as the full length of the permanent magnet blocks when assembled onto the magnet base. This was done to ensure that there was even pressure along the full length of the poles and permanent magnet blocks during the curing process.

The pusher bar 240 is similar to the end stop except it has holes to allow it to be screwed to push against and hold the permanent magnet blocks end to end during the curing process.

The method used for assembling the hybrid magnetic structure of Example 1 comprises the steps of:

Step 1: Mount the magnet base 110 into the bonding fixture base 230 using four socket head screws. Place non-magnetic shims around the perimeter of the magnet base to prevent mis-alignment of the base relative to the bonding fixture base during the assembly process. It is also important to clean all magnetic structure parts immediately prior to assembly with acetone or other volatile solvent to insure bond integrity.

Step 2: Install the end stop 240 onto the bonding fixture base so that it is perpendicular to the slots in the magnet base 110 and is in the right position to symmetrically locate the blocks of permanent magnet material 130 in the base.

Step 3: Place a thin coating of epoxy on the $1^{st}$, $3^{rd}$, $5^{th}$, $7^{th}$ and $9^{th}$ slots of the magnet base 110 and loosely install the lower magnet clamp over the base. Do not tighten the retaining screws.

Step 4: Place a thin coat of epoxy on the lower surfaces of one 1.875" long permanent magnet block and slide it into the first slot of the base and lower magnet clamp. Use care to avoid applying any epoxy on the upper surfaces of the block as this may cause the block to bond to the fixture. Adjust the magnet clamp so that the permanent block slides freely into the slot. Repeat the operation by sliding a magnet into the $9^{th}$ slot and making any further adjustments of the magnet clamp to allow smooth insertion of the second magnet block. It is important to remember the anisotropic orientation of the magnet blocks in this stage of the assembly must be in the same direction as shown by the arrows 170 on the ends of the blocks as shown in FIG. 3.

Step 5: Insert three more 1.875" permanent magnet blocks with epoxy coating into the center alternating slots followed by five of the 0.800" long permanent magnet blocks. Lightly clamp the blocks using vertical set screws if necessary to control any magnetic interactive forces.

Step 6: Insert the remaining five 1.875" permanent magnet blocks with epoxy coating into the slots. Clamp the blocks using vertical set screws in their approximate final location. Install the pusher bar, aligning the screw holes so that pusher screws can be tightened directly (horizontally) against the end of the permanent magnet blocks. Loosely tighten the pusher screws against the end of the permanent magnet blocks. Loosen the vertical set screws and firmly tighten the horizontal pusher screws to force the magnet blocks tightly against each other in each of the five slots. Verify that they are correctly positioned by looking through the view slots in the lower magnet clamp. The exposed ends of the last permanent magnet blocks should be aligned with each other to within approximately 0.020".

Step 7: Place the lower magnet clamp over the width of the base and the permanent magnet blocks. Screws are inserted vertically onto each permanent magnet block. Tighten screws on the lower magnet clamp and then tighten all vertical set screws to insure that the magnets are firmly seated in their slots. Do not over tighten.

Step 8: Leave all clamps tightened and allow this stage of assembly to cure a minimum of four hours before proceeding to the next step.

Step 9: After cure, remove all clamps and remove any excess epoxy from the structure. Carefully clean the remaining four empty permanent magnet slots (slots 2, 4, 6 and 8) of any cured epoxy or debris.

Figure 6A:
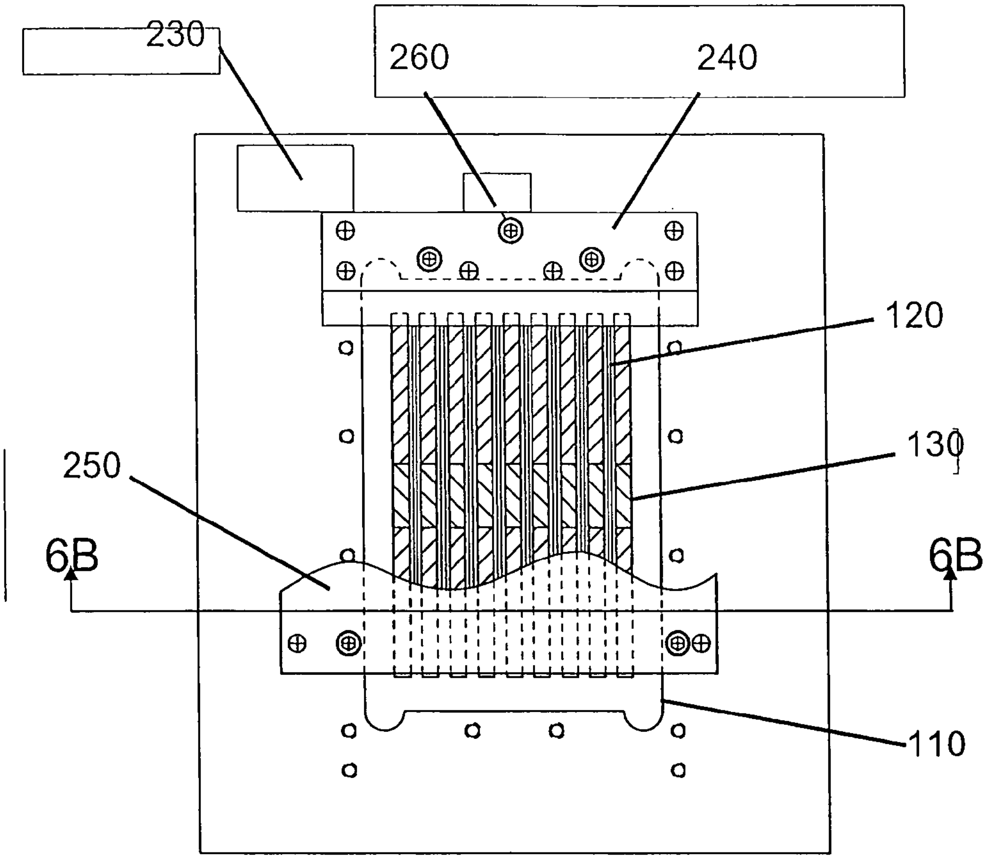
FIG. 6 is a top view (FIG. 6A) and a cross-sectional view (FIG. 6B) of a preferred hybrid magnetic structure during assembly secured by bonding fixtures.
Figure 6B:
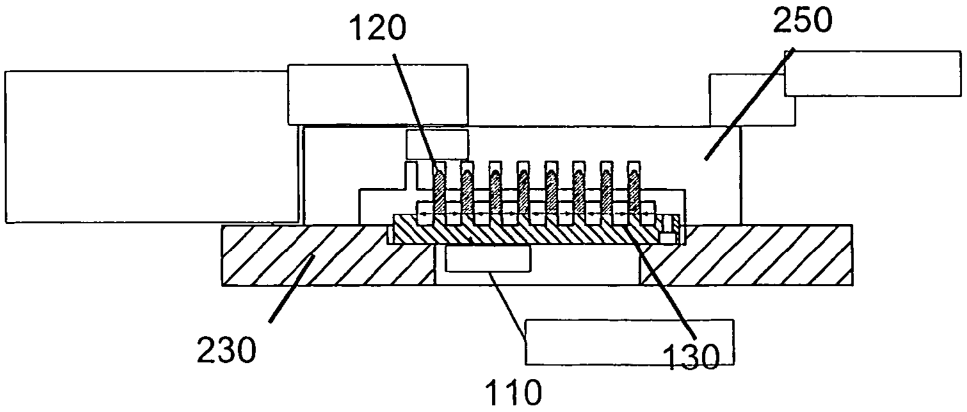
Figure 7:
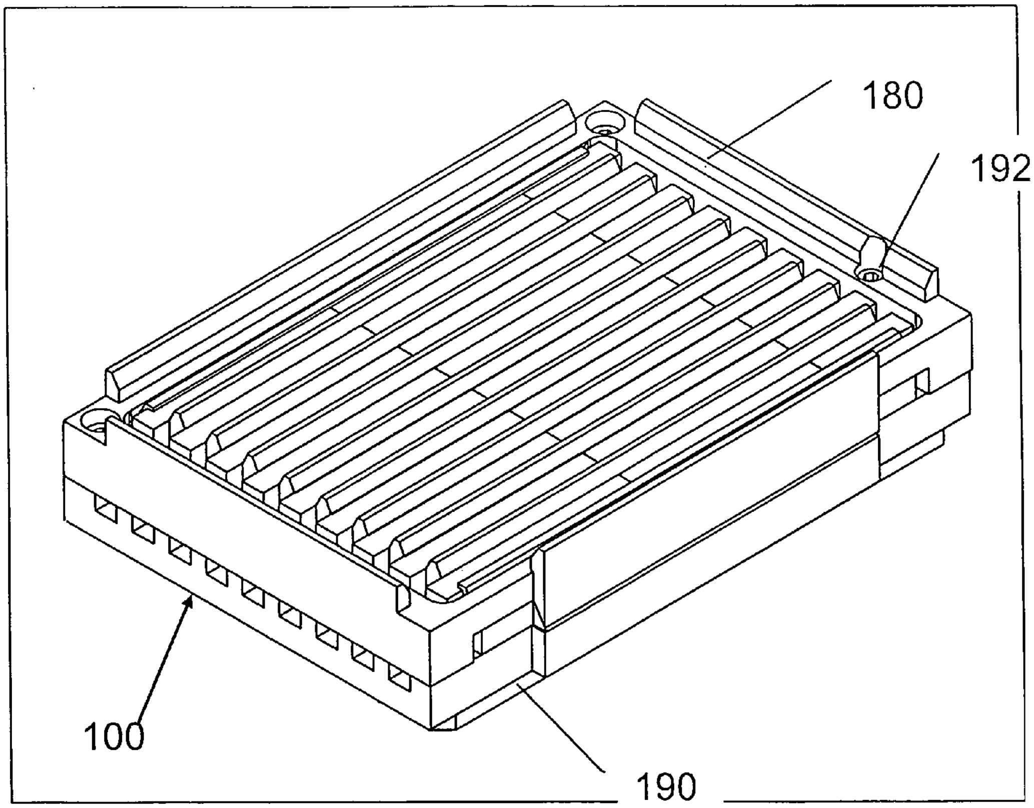
FIG. 7 is a perspective view of a preferred hybrid magnetic structure assembled with microtiter plate interface and lower locator plate for use with liquid handling robots and systems.

Step 10: Repeat steps 2 through 8 to fill the remaining four slots in the magnet base as described previously. The permanent magnet blocks in step 10 must be oriented in the opposite direction to those inserted in the previous five slots. FIG. 3 and FIG. 6B show the correct orientation of the permanent magnetic blocks in relation to each other and to the magnet base.

Step 11: After cure, remove all clamps and remove any excess epoxy from the structure. Carefully remove any epoxy from between the magnets to allow for proper seating of the poles.

Step 12: Install the end stop so that it is positioned to center the poles on the magnet base.

Step 13: Rough up the sides of the nickel-plated ferromagnetic poles with medium grit emory cloth prior to installation to insure good epoxy adhesion. DO NOT disturb the plating on the actual pole tips.

Step 14: Place a thin coat of epoxy on the lower surfaces of the ferromagnetic poles and in the slots formed by the lower array of magnet blocks. Carefully lower the poles into these slots and position them against the end stop 240. Verify that they are longitudinally centered relative to the magnet base. Strong magnetic forces will hold the poles in place during the cure. Use care to avoid applying any epoxy on the upper surfaces of the poles as this may cause the poles to bond to the fixture.

Step 15: Install the pole alignment clamp 250 over the newly installed poles before any curing of the epoxy has taken place. This will require some downward pressure by hand or by means of the mounting screws for this fixture. FIG. 6A shows the top view of a magnet base 110 secured to a bonding fixture base 230, with the end stop 240 and the pole alignment clamp 250 secured by various types of screws 260. FIG. 6B shows a cross-sectional view to show how the alignment of the ferromagnetic poles in relation to the pole alignment clamp, the magnet base and first set of permanent magnet blocks.

Step 16: Tighten the mounting screws of the pole alignment clamp and allow poles to cure for a minimum of four hours.

Step 17: After cure, remove all clamps and remove any excess epoxy from the structure. Carefully remove any epoxy from between the poles to allow for proper seating of the next layer of permanent magnet blocks.

Step 18: Repeat steps 2 through 8 to install the upper layer of permanent magnet blocks in slots 2, 4, 6 and 8 of the structure. Use the upper magnet clamp fixture for this process and invert the end stop so that it is aligned with the upper layer of magnets. It is important that the magnets in step 18 and 19 be oriented in the same direction as those in the slots immediately below them.

Step 19: After minimum 4 hour cure time, repeat step 18 to fill the 3rd, 5th and 7th slots leaving the two end slots for last.

Step 20: After removal of all prior fixtures and clean-up, install the two magnet retainers loosely on the magnet base.

Step 21: Install the end stop on the bonding fixture base.

Step 22: Coat the 1st and 9th slots formed by the magnet retainers and the ferromagnetic poles with a thin coat of epoxy and then install the side clamp fixtures. Large screws should secure the side clamps to the bonding fixture base and against the magnet base.

Step 23: Coat the sides and bottom surface of the permanent magnet blocks with a thin coating of epoxy and slide them into the 1st and 9th slots. Clamp the permanent magnet blocks against the end stop by tightening the vertical and horizontal set screws of the side clamps iteratively. This will tightly press the magnets against the poles and down onto the existing magnets below. Make sure the permanent magnet blocks in step 23 are oriented in the same direction as those in the slots immediately below them.

Step 24: Tighten the retainer mounting screws and allow the structure to cure for a minimum of 4 hours.

Step 25: After curing, remove all fixtures, clean off any residual epoxy, coat the upper surfaces of the structure with a thin, uniform coating of epoxy and allow to cure for 8 hours minimum prior to use

EXAMPLE 5

Removable Microtiter Plate Interface for High-Throughput Lab Workstation Robots

Figure 12C:
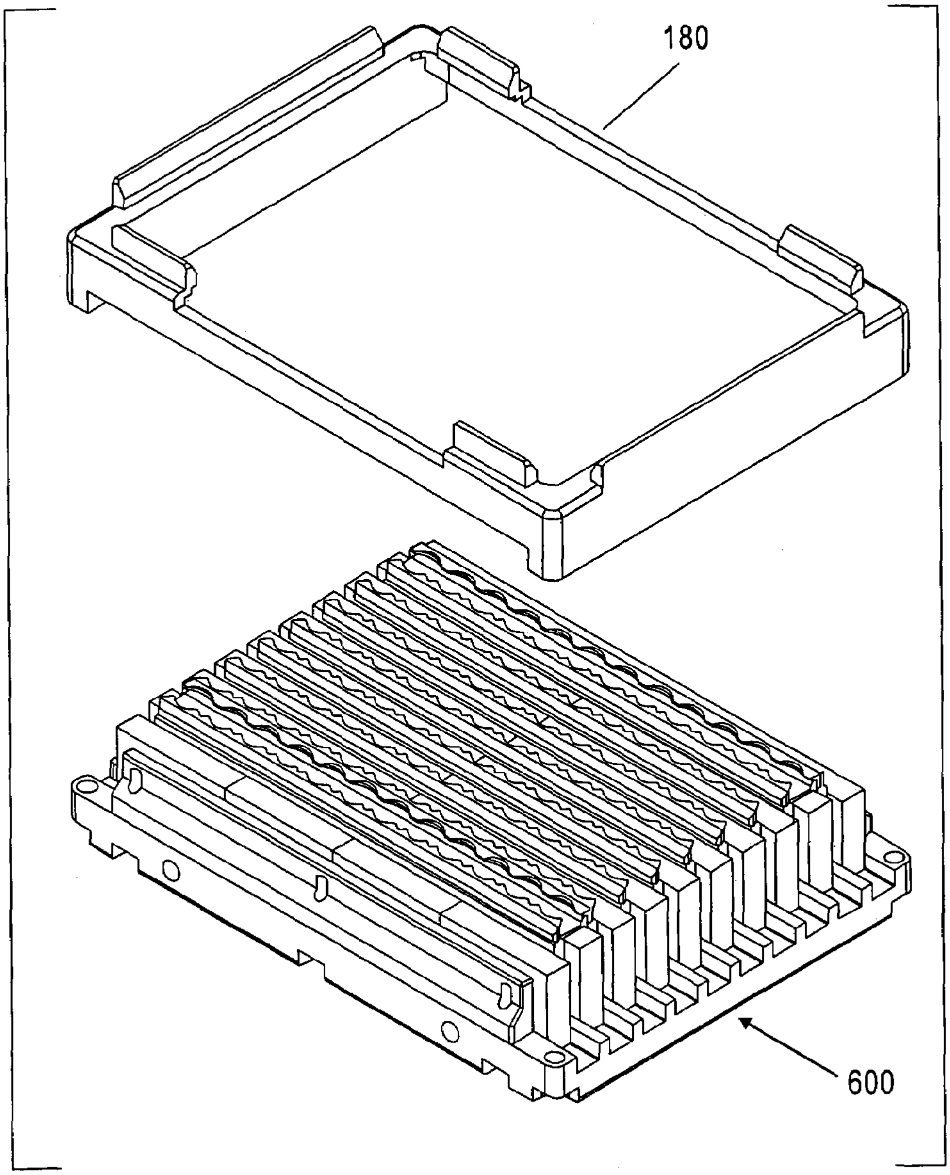
FIG. 12C is an exploded view of the assembled hybrid magnetic structure and an upper interface for use with a BIOMEK robot.

Referring now to FIG. 12C, the removable microtiter plate interface 182 was fashioned from aluminum 6061-T6 and clear anodized. The machine shop was instructed to finish to 63 RMS, break edges 1/64, and break corners 1/32. The interface is a rectangular bracket fitted to the hybrid magnetic structure 100 of Example 1. On each of the two ends of the interface are two holes for screws that attach the interface 182 to the base plate 110.

This interface 182 is meant to be used with robots that have arms or pipette heads with microtiter plate grippers that move in the X, Y and Z directions, as opposed to robots that have elevator platforms that move only up and down along the Z or vertical axis. The BIOMEK® FX Lab Workstation (Beckman-Coulter, Fullerton, Calif.) is one example of an available robot used to carry out high throughput protocols and processes which has pipette heads with microtiter plate grippers that move in the X, Y and Z directions.

The removable microtiter plate interface 182 provides ramps as a means for the robot to accurately place the microtiter plate 210 onto the hybrid magnetic structure so that the liquid handling head on the robot can precisely place the 96- or 384-pipette tips 220 into the microtiter plate wells and to keep the microtiter plate 210 perfectly positioned on the hybrid magnetic structure 100 throughout the process.

EXAMPLE 6

Interface for Single-Axis Liquid Dispensing Robots

Figure 8:
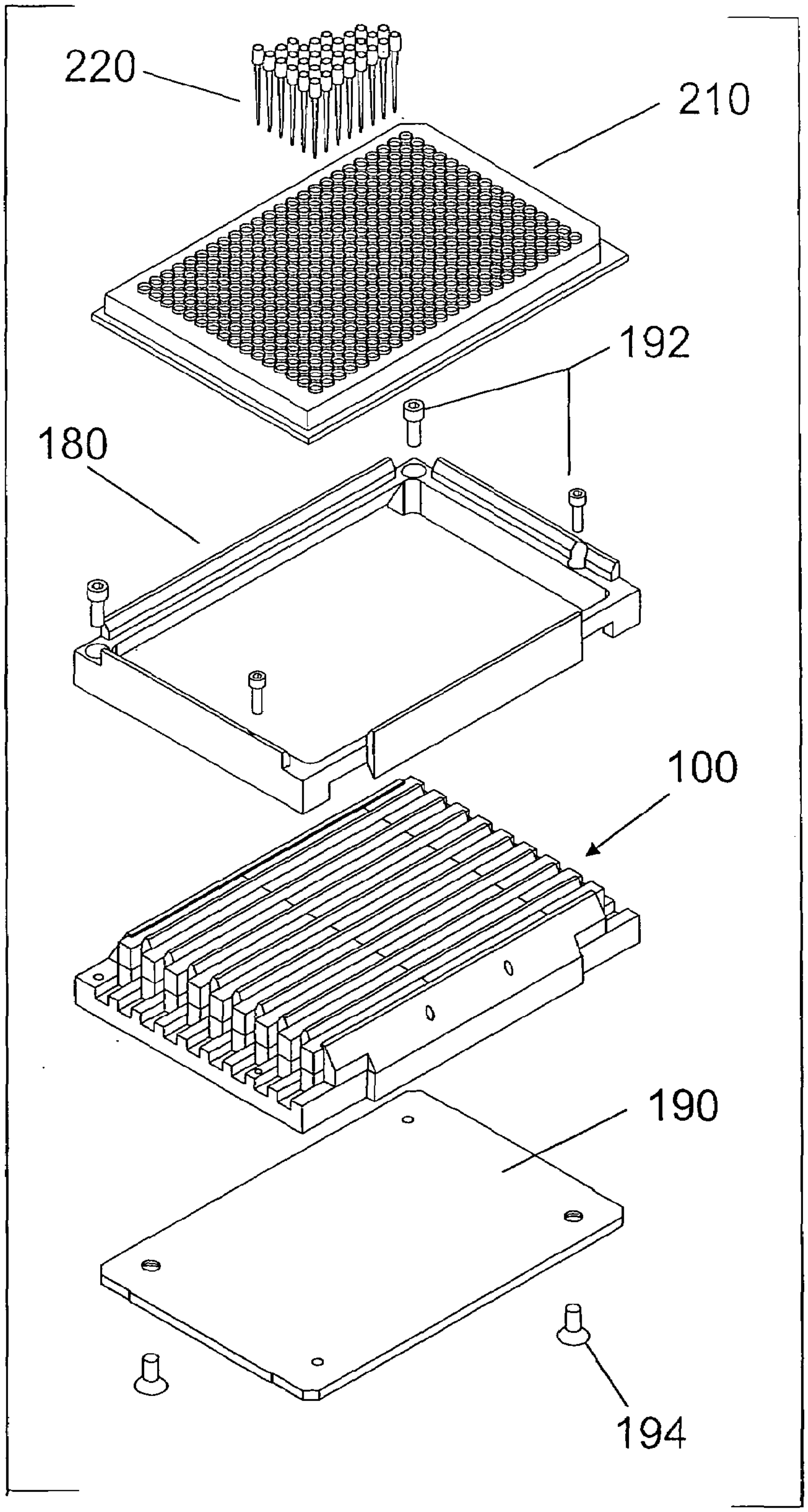
FIG. 8 is an exploded view of the preferred hybrid magnetic structure assembled with the microtiter interface, lower locator plate, and fasteners which hold the assembly together. A microtiter plate and a partial array of disposable tips for liquid handling are shown.

Referring now to FIG. 8, a Microtiter Plate Interface 180 for a Single-Axis Robot was fashioned from aluminum and clear anodized. The machine shop was instructed to finish to 63 RMS. The interface 180 is a rectangular bracket fitted to the hybrid magnetic structure 100 of Example 1. Four holes enable the interface to be fastened on top of the hybrid magnetic structure 100 by fasteners 192 and special perimeter shaping allows for movements within certain dispensing robots.

This interface 180 is meant to be used with single-axis robots that have elevator platforms that are stationary in the X-Y or horizontal plane, although the platform moves up and down along the Z or vertical axis. The HYDRA-384® (Robbins, Sunnyvale, Calif.) is one example of such a robot used to carry out high throughput liquid micro dispensing, which moves the elevator platform only in an up and down direction.

The removable microtiter plate interface 180 for single axis robots provides ramps as a means for an operator to accurately place a microtiter plate 210 onto the hybrid magnetic structure on the elevator platform of the robot so that the liquid handling head on the robot can precisely place the 96- or 384-syringe needles into the microtiter plate wells. The interface 180 also acts as means to maintain clearance of the other moveable and stationary parts of the robot and to keep the microtiter plate perfectly positioned on the hybrid magnetic structure to prevent the needles from "crashing" into the microtiter plates 210 due to misalignment of the microtiter plate.

EXAMPLE 7

Lower Locator Plate for Single-Axis Robots

Referring to FIG. 8, the lower locator plate 190 was made of aluminum, 2.6"×5.05" and 0.125" thick, then attached beneath the hybrid magnetic structure 100 through fasteners 194. The lower locator plate 190 allows the hybrid magnetic structure 100 to be seated snugly onto the microtiter plate platform of robots and precisely positioned in the X-Y or horizontal plane. These robots may have a platform that elevates plates so that the arrayed head of needles can deposit, mix, touch or draw out precise micro volumes. Since each needle in these types of robots is connected to a calibrated syringe, and replacement and disassembly is very costly and laborious, it is important to prevent the needles from "crashing" into the microtiter plates 210 due to misalignment on the elevator platform.

EXAMPLE 8

Scaling up the Hybrid Magnetic Structure to Increase Field Strength

A novel feature of the hybrid magnetic structure is that it is scalable and thus the field strength can be increased. Unlike the available magnetic devices which are limited to their design, the increase in height of the soft ferromagnetic poles 120 and the blocks of permanent magnet material 130 will increase field strength.

EXAMPLE 9

Modification of the Ferromagnetic Poles for Specialized Function

Referring now to FIG. 10, poles 120 of the hybrid magnetic structure 200 can be easily machined to achieve complicated shapes that produce complex field distributions while maintaining high fields and strong gradients. FIG. 10B shows a cross-sectional view of a "T-" shaped, variant cross-section of the soft ferromagnetic poles 120 that produces concentrated, transverse gradient fields at elevated locations on the microtiter plate wells. An array of wells 210 is shown in relative position to the poles 120.

The top view in FIG. 10A shows the circular cutouts 128 in the top of the poles that conform to the well shapes of thermal cycler or "PCR" microtiter plates and provide a crescent shaped, gradient force field at the upper portion of the T-shaped pole at an arbitrary height on the well. The T-shaped ferromagnetic poles 120 allow magnetized material in solution, e.g., DNA, to be held above the bottom of the wells while solutions are completely extracted by means of aspiration devices without disturbing the held, magnetized material.

Notice also that the outside soft ferromagnetic poles 120 (2 out of 9 of the soft ferromagnetic poles) are of a specialized inverted L-shape to maintain the same crescent-shaped fields on the peripheral wells of the microtiter plate 210.

EXAMPLE 10

DNA Separation

The common method for DNA clean-up and separation using magnet plates is generally the following steps: (1) Carboxylate-coated ferrite beads are mixed with solution containing DNA to be separated from solution, thereby allowing beads to bind to receptor locations on DNA to magnetize DNA. (2) The microtiter plate containing magnetized DNA is placed on a magnetic structure allowing magnetic field exertion over the solution. The gradient in magnetic fields will cause the magnets and DNA to move toward the field and hold it against a region of the well. This allows the extraction of the rest of the solution through a liquid handling mechanism, leaving behind the magnetized DNA. (3) The magnetized DNA is washed with EtOH, or other wash solution, repeatedly either by vortexing or pipet agitation. The wash solution is extracted to leave a pellet of magnetized DNA remaining in microtiter plate wells. (4) The DNA is resuspended in water or other solution and mixed to cause the beads to release the DNA. (5) The microtiter plate containing DNA is again placed on a magnet plate and the ferrite beads will be held at side or bottom of well. The suspended DNA is removed or aspirated and ready to be sequenced, electrophoresed or used for other applications.

EXAMPLE 11

High-Throughput Method Using the Hybrid Magnetic Structure, Tailored for Robotic Platforms and Capillary Electrophoresis Instruments A high-throughput method to purify DNA sequencing fragments was created using magnetic beads previously used to purify template DNA for sequencing. Because of the high performance of the hybrid magnetic structure, for example, in faster draw-down and holding power, high-throughput protocols featuring the hybrid magnetic structure can be created. One such example—the method of magnetic bead purification of labeled DNA fragments for high-throughput capillary electrophoresis sequencing, which has been demonstrated to result in a 93% pass rate and an average read length of 620 phred20 bases, which arguably surpasses most other methods.

This method binds crude DNA to carboxylated magnetic particles with a solution of polyethylene glycol and sodium chloride. The beads were washed multiple times with 70% ethanol and pure DNA was eluted with water. While this method met the requirements listed above, a technique was needed that worked in 384-well PCR plates and produced extremely pure DNA.

A search was made for a low viscosity, highly soluble binding buffer that had a negligible impact on electrophoresis trace quality. To solubilize the dyes in the sample and desalt and precipitate DNA, a highly polar substance that could be easily washed out with both water and ethanol was needed. Other desirable properties included low viscosity, neutral charge, liquid phase at room temperature, solution density greater than water to encourage mixing, low toxicity and high stability. Tetraethylene glycol best fit this criteria. Various combinations of TEG and ethanol were tested for labeled ssDNA yield and sequencing trace quality. The optimal range was quite large at 50±10% ethanol with 5% TEG as compared to 70±3% range for ethanol precipitation. Preparation of template DNA by the rolling circle mechanism (RCA) results in an essentially pure sample because large RCA template bind almost irreversibly to magnetic beads (C. Elkin, H. Kapur, T. Smith, D. Humphries, M. Pollard, N. Hammon, and T. Hawkins, "Magnetic Bead Purification of Labeled DNA Fragments for High Throughput Capillary Electrophoresis Sequencing", *Biotechniques,* Vol 32, No. 6, June 2002, pp 1296-1302.).

To prepare for the smaller 384-wells, volumes and wash steps were reduced. The major concern was to keep the small amount of magnetic beads in the microtiter plate wells during aspiration and washing. The hybrid magnetic structure of Example 1 (as shown in FIGS. 1 and 2) and interface for the 384-well plates were designed and made because currently available magnet plates produced weak fields and gradients, poor results and long separation times. Also many are not capable of being used with 384-well microtiter plates. Furthermore, those magnet plates that are compatible with 384-well microtiter plates require longer contact time, which in turn adds unwanted time to automated protocols.

The hybrid magnetic structure of Example 1, coupled with a Robbins Scientific 384 syringe HYDRA® (Sunnyvale, Calif.) resulted in an excellent manual process that has produced over 800,000 samples with 91% averaging 605 phred20 bases, thus far. The protocol was then transferred to the BIOMEK® FX Lab Workstation, a robotic platform manufactured by Beckman Coulter (Fullerton, Calif.). Initially, other robotic platforms with steel tips were tested and it was discovered that the hybrid magnetic structure induced a magnetic field in the tips which resulted in bead loss and subsequent low yields of labeled ssDNA. Therefore, polypropylene pipette tips that could be washed and reused were used. To eliminate the use of plate seals, TEG ethanol concentrations were optimized to minimize evaporation effects associated with plates remaining uncovered for up to one hour. The steps of pipette mixing to eliminate vortexing and plate movement steps were also added.

These automated systems eliminated 75% of the labor required for ethanol precipitation while maintaining reagent costs at $0.005 per sample. A forty base pair increase in the facility's phred20 average read-lengths was noted as a result of this new method. Elimination of centrifugation reduced the risk of ergonomic injuries resulting from the loading and unloading of centrifuges. The substitution of water for formamide buffer eliminated the exposure to this teratogen toxin and ethanol consumption was reduced 400% eliminating fire hazards and waste disposal issues. A BET (as in Beads, Ethanol and TEG) stock solution is made beforehand using the following recipe to process twenty 384-well plates: 64.0 mL Ethanol (100%), 7.0 mL deionized water, 6.4 mL Tetra Ethylene Glycol, and 2.0 mL Carboxylated Beads (5% solids.0.8 um dia.). The following is the current protocol optimized for use.

Sequencing Fragment Purification Protocol

1. Sequence RCA generated DNA template is reduced to final volume of 5 μl in a 384-well PCR plate.
2. Add 10 μL of BET solution to each well. Verify solution is mixed thoroughly. Mix by pipetting or vortex as needed. Incubate at room temperature for 15 minutes to allow beads to bind to DNA template.
3. Place 384-well plate on a hybrid magnetic structure for 1 minute.
4. Place 384-well plate/hybrid magnetic structure assembly on Robbins HYDRA® 384 and aspirate solution.
5. Add 15 μl of 70% ethanol solution to each well.
6. Place 384-well plate/hybrid magnetic structure assembly on HYDRA® 384 platform and aspirate solution. Air-dry samples for 10 minutes or continue to step 10.
7. Dispense 15 μL of deionized water to each plate. Mix by pipetting or vortex until beads are resuspended. Remove 384-well plate from hybrid magnetic structure.
8. Incubate 10 minutes at room temperature to allow beads to release bound DNA.
9. Place 384 well microtiter plate on hybrid magnetic structure for 2 minutes.
10. Transfer 10 ul of water solution to suitable PCR plate for electrokinetic injection.

This automated purification protocol has produced over 800,000 samples with 93% averaging 620 phred20 bases, which makes for a highly reliable 384-well method that is well-suited to industrial scale DNA purification and sequencing.

EXAMPLE 12

Pathogen Testing

Several companies produce magnetic and paramagnetic beads which aid in the identification of food and fluid-borne pathogens such as *Listeria, E. coli, Cryptosporidium, Staphylococcus* and *Salmonella*. For example, Dynal Biotech (Lake Success, N.Y.), produces super paramagnetic beads covalently coated with affinity purified antibodies against specific surface markers on the microorganism. The beads are supplied as a suspension in phosphate buffered saline (PBS), pH 7.4 with 0.1% (human or bovine) serum albumin (HSA/BSA) and 0.02% sodium azide and require a magnet for the assay. Improvement in field strength and the magnetic gradient distribution by using the hybrid magnetic structure would improve separation and assay detection time and accuracy. Efficient and powerful use with 384-well plates will increase the number of different strains that can be tested at one time, thereby also resulting in faster detection time.

EXAMPLE 13

Using the Hybrid Magnetic Structure for Molecular Manipulation

Referring now to FIG. 11A, which shows the single pole embodiment 300 of the hybrid magnetic structure, an application of single-molecule experiments is also contemplated by this invention. The strong magnetic fields created at the pole tip of the ferromagnetic pole can be used to manipulate and apply forces to biomolecules that are tethered to magnetic beads. The hybrid magnetic structure can be used to apply torsional stress to individual DNA molecules as suggested by work described in Smith, S. B., Finzi, L. & Bustamante, C., *Science* 258, 1122-1126 (1992) or Strick et al, *Science* 271, 1835-1837 (1996) and *Nature* 404, 901-904 (2000).

For example, a single strand of DNA is tethered at one end to a microscope slide. The un-tethered end of strand is attached to a magnetic bead. A magnetic field is applied using the hybrid magnetic structure 300. The hybrid magnetic structure 300 is firmly attached to a rotating platform or disk, such as a rotating turntable. The center of the rotating platform is fixed. The molecule tethered to the slide is placed at the fixed point. An optical microscope is placed under the slide and a light source above the turntable to monitor and detect the DNA strand. The turntable is turned about the fixed point, controlled by an automated drive system, which controls rotation speed and number of revolutions.

The hybrid magnetic structure 300 creates a force vector that acts on the magnetic bead. The hybrid magnetic structure 300 also creates a magnetic field that has a separate field vector. The force vector creates a pull force on magnetic bead, while the magnetic field vector fixes the orientation of the magnetic bead by aligning its dipole axis in the direction of the field vector at that point. This prevents the bead from rotating in the field. The entire molecule is rotated and twisted or untwisted. Axial forces stretch the DNA molecule and fixing forces create twisting/tortional forces on the molecule. Varying the proximity of the hybrid magnetic structure 300 to the magnetic bead also varies the force acting on the bead and molecule.

These types of studies will yield information about the forces that hold biomolecules together and the mechanics of molecular motors. These single molecule manipulations can be performed on other types of molecules, including but not limited to RNA, proteins, membrane-bound proteins, protein complexes, and polymerized proteins like actin filaments.

EXAMPLE 14

Phage Display Against Targets

The use of phage display in screening for novel high-affinity ligands and their receptors has been useful in functional genomics and proteomics. Phage display works by creating a phage displayed library and then exposing this library to a target. The unbound phage particles are washed away, while the phage particles that are bound to the target are then dissociated from the target and replicated.

Referring now to FIG. 11B, the hybrid magnetic structure 400 can be used in an experimental strategy to use targets that are attached on magnetic beads. These protocols are generally carried out using microcentrifuge tubes. After the phage is isolated from cells, and then incubated with magnetic beads, the microcentrifuge tube can be placed in the center of a hybrid magnetic structure 400 to immobilize the magnetic beads and separate the bound phage and target from the unbound phage in solution.

EXAMPLE 15

Hybrid Magnetic Structure Used in Bioorganism Indicators

Referring now to FIGS. 11C and 11D, using the hybrid magnetic structure 500 for specific detection of bioorganisms, such as the *Bacillus* species, provides a tool for defining the success or failure of a sterilization process. One such detection method is using antibody-coated paramagnetic beads. The beads are mixed and incubated with the solution in question. The beads bind to various cellular materials with specificity before being loaded onto a column which is then placed into the center of a hybrid magnetic structure 500. The column is washed until the flowthrough is clear. The excess antibody is washed off while the magnetically labeled cells remain in the column. The retained fraction can then be eluted from the column to recapture and count the labeled cells.

Use of the hybrid magnetic structure 500 will increase the field strength and the holding power of the magnets. The number of labeled cells that pass through and are not held by the magnet in the column will decrease, thereby increasing the accuracy of the assay.

EXAMPLE 16

Hybrid Magnetic Structure Having Asymmetrical Poles Featuring Notches and Cutouts for Use with Multi-Well Containers Having Round or Conical Wells A hybrid magnetic structure for use with specific types of multi-well containers can be made. Referring now to FIG. 12A, a hybrid structure 600 can be made for use with microtiter plates such as 96-well thermal cycler plates or round-bottom plates are used. PCR plates are characterized by small conical-shaped wells and used for carrying out PCR and sequencing reactions in thermal cycler devices. Round-bottom microtiter plates have large round-bottom wells often for carrying out inoculations and cell culture. As shown in FIG. 12B, the pole tip 124 of this hybrid structure 600 is asymmetrical in its cross-section (FIG. 12B.4), and has small notches 126 in the pole between each large cutout 128 for the round wells (FIG. 12B.3) and a chamfer 129 for contouring the wells of the microtiter plate. The notches and cutouts can vary in shape, diameter and the distance away from the center line of the pole. These assembled hybrid structures can be used in conjunction with an upper interface 180 (shown in FIG. 12C) and lower locator plate (not shown).

Figure 12D:
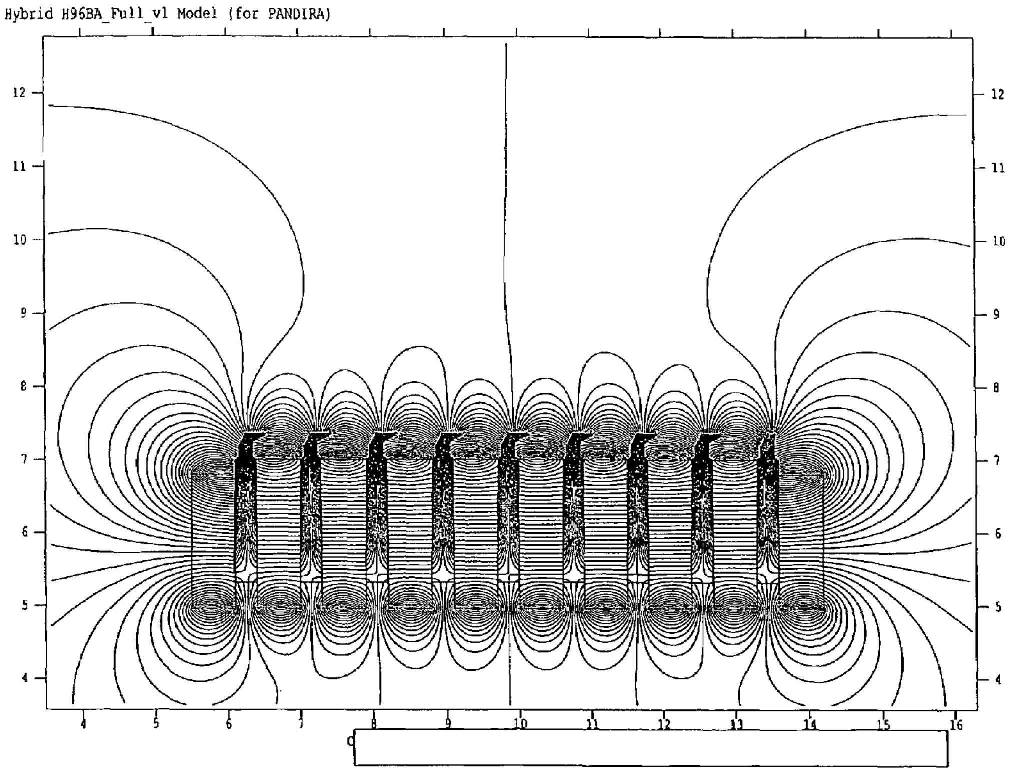
FIG. 12D is two-dimensional modeling of the asymmetric pole hybrid magnetic structure using PANDIRA.

Based on the computer model shown in FIG. 12D, this structure should feature field levels of 1.1 to 1.2 Tesla or greater at the pole tip (data not shown). The field distributions generated by this structure are shown in FIG. 12D.

EXAMPLE 17

Figure 13C:
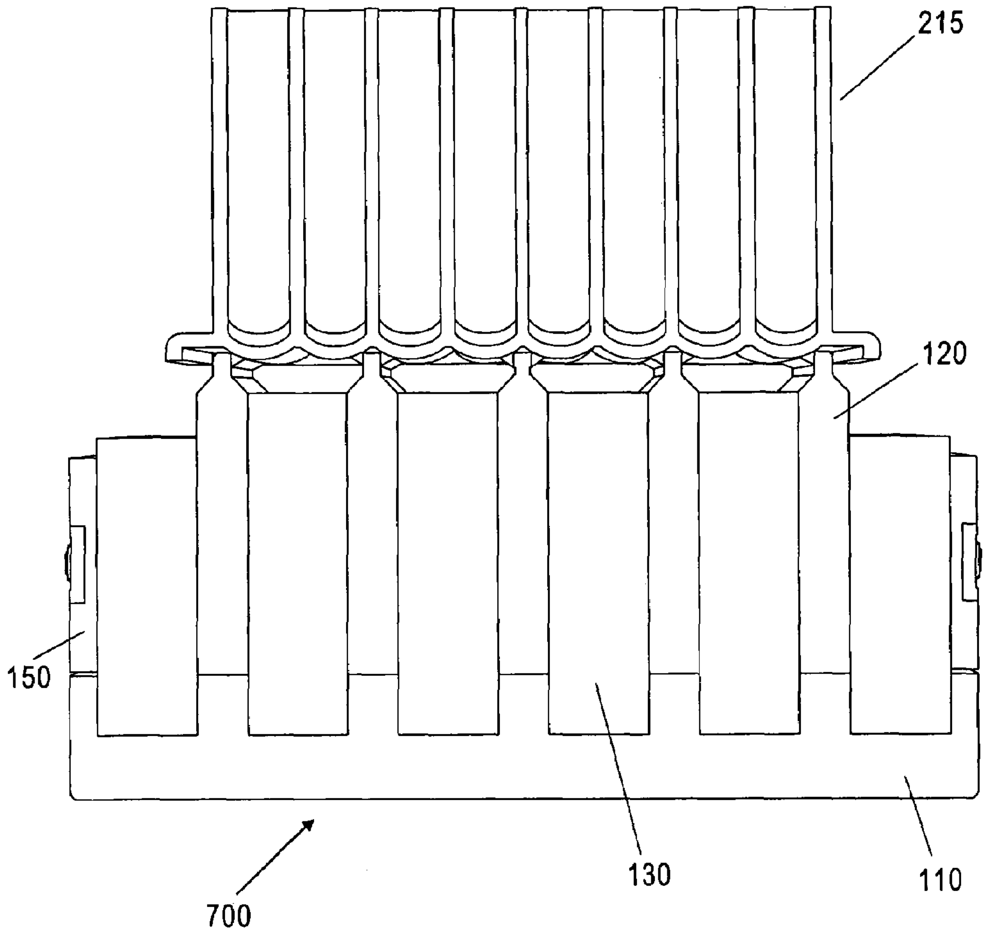
FIG. 13C is a cross-sectional view of the long period hybrid magnetic structure with a deep well container seated above the structure.

Long Period Hybrid Magnetic Structure Having Asymmetrical Poles Featuring Notches and Cutouts and Retainer Rods for Use with Multi-Well Containers Having Deep Wells FIG. 13C is a cross-sectional view of the long period hybrid magnetic structure with a deep well container seated above the structure.

Referring now to FIG. 13, a long period hybrid magnetic structure 700 can be made for use with deep well containers 215, such as Beckman "deep well blocks", which hold up to 2 mL of culture. FIG. 13A is a perspective view of the assembled long period hybrid magnetic structure. These hybrid structures can also be used in conjunction with an upper interface and lower locator plate or these larger volume multi-well containers can be simply seated directly onto the assembled hybrid magnetic structure as shown in FIG. 13C. Because the amount of fluid to be acted on is larger, the magnetic fields of the hybrid magnetic structure must reach farther up above the pole tips into the deep well containers. Thus, the hybrid magnetic structure is scaled up by a factor of 2 to increase the extension of the magnetic field and maintain gradient strength.

The internal forces of the long period hybrid magnetic structure are greater and suggest a more efficient assembly method than the epoxy and retainers of the hybrid magnetic structure 100 to hold the structure together. FIG. 13B is an exploded view of the long period hybrid magnetic structure 700 featuring well cutouts 128 in the ferromagnetic poles 120 and retainer rods 140 to hold the assembly together. Retainer rods 140 of aluminum can be made to internally hold the assembly together. Circular cutouts in the poles and blocks can be made to fit retainer rods through so the retainer rods can be secured to the retainers 150 through a fastening means 160. The retainer rods 140 are preferably inserted through a section of the pole 120 having less or unsaturated flux so as not to interfere with the internal flux distribution and inadvertently decrease performance and gradient strength.

Note for both structures that the outside blocks of permanent magnets can be lower in height than the internal blocks of permanent magnets in order to accommodate unique microwell plate structures. For example, Beckman "deep well blocks" 215 feature a large overhang outside of the wells and in order to seat the deep well container securely and closely to the hybrid magnetic structure, the outside blocks of permanent magnet are shorter to accommodate the large overhang.

Figure 13D:
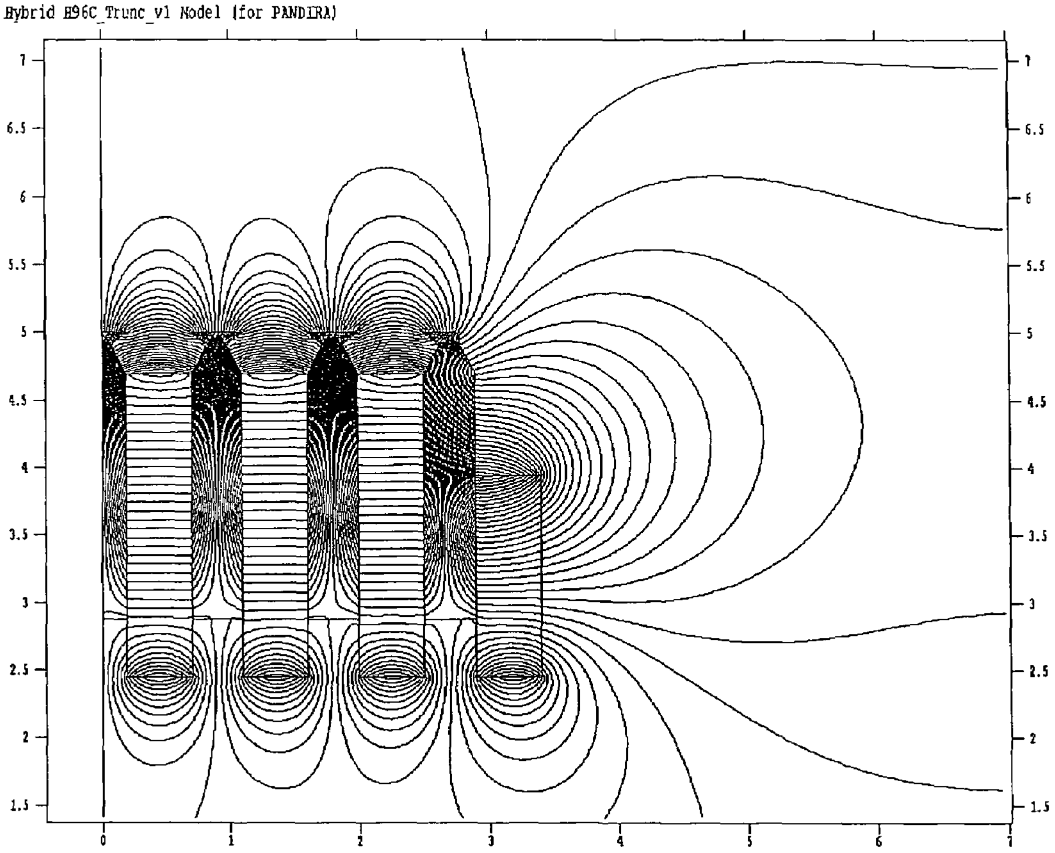
FIG. 13D is two-dimensional modeling of the long period hybrid magnetic structure using PANDIRA.

Based on the computer model shown in FIG. 13D, this structure should feature field levels of 1.1 to 1.2 Tesla or greater at the pole tip (data not shown). The field distribution generated by this structure is shown in FIG. 13D.

EXAMPLE 18

Hybrid Magnetic Structure Having a Return Yoke

Referring now to FIG. 14, a hybrid magnetic structure 800 with an even number of poles can be made having a return yoke 250 outside the non-magnetic base 110. The return yoke 250 is comprised of steel or high permeability ferromagnetic steel, to be used for shielding and as a flux conduit. The outer permanent magnets have their magnetization orientations facing in the same direction and the return yoke covers the entire side surface area of the outer blocks of permanent magnet material. The bottom of the core hybrid magnetic structure components of the poles 120 and permanent magnet blocks 130 is shown to have a sufficient distance of about 0.5 inches from the return yoke 250 to avoid fields in the lower parts of the structure from being shunted to the return yoke. The return yoke 250 also acts as shielding to minimize stray fields below the structure.

EXAMPLE 19

Compact Hybrid Magnetic Structure with Non-Uniform Shaped Poles

Referring now to FIG. 15, a compact hybrid magnetic structure 900 can be made using non-uniform wedge-shaped ferromagnetic poles 120 and permanent magnet blocks 130. This creates compactness in the hybrid magnetic structure and can also improve tuning of the field distribution for non-periodic effects.

The present structures, embodiments, examples, methods, and procedures are meant to exemplify and illustrate the invention and should in no way be seen as limiting the scope of the invention. Various modifications and variations of the described hybrid magnetic structure, methods of making, and applications and uses thereof of the invention will be apparent to those skilled in the art without departing from the scope and spirit of the invention.

Any patents or publications mentioned in this specification are indicative of levels of those skilled in the art to which the invention pertains and are hereby incorporated by reference to the same extent as if each was specifically and individually incorporated by reference.

What is claimed is:

1. A hybrid magnetic structure comprising:

a. a non-magnetic base;

b. a ferromagnetic pole;

c. at least two blocks of permanent magnet material; and d. a return yoke;

wherein the at least two blocks of permanent magnet material are assembled onto said base on opposite sides of and adjacent to said ferromagnetic pole, in a periodic array, and have the magnetization orientations oriented in opposing directions and orthogonal to the height of said ferromagnetic pole, and wherein said blocks of permanent magnet material extend below the bottom edge of said ferromagnetic pole when assembled onto said base; and, wherein the ferromagnetic pole has a shaped tip which extends in a longitudinal direction from a bottom edge to a shaped tip which extends beyond each block of permanent magnet material and wherein said shaped tip is shaped to allow close proximity with a containment vessel.

2. The hybrid magnetic structure of claim 1, further comprising two ferromagnetic poles, one on each end of said periodic array.

3. The hybrid magnetic structure of claim 1, further comprising at least one retainer adjacent the outermost block of magnetic material.

4. The hybrid magnetic structure of claim 1, further comprising a pair of opposing retainers extending orthogonally to the magnetization orientation.

5. The hybrid magnetic structure of claim 1, having a magnetic field strength of at least 6000 Gauss.

6. The hybrid magnetic structure of claim 1, wherein said shaped tip has notches to adjust the field gradient produced.

7. The hybrid magnetic structure of claim 1, wherein said shaped tip features a chamfer allowing the pole to contour the shape of the containment vessel and maintain close proximity.

8. The hybrid magnetic structure of claim 7, wherein said shaped tip is within 1-2 mm of the containment vessel.

9. The hybrid magnetic structure of claim 1, wherein the non-magnetic base is aluminum.

10. The hybrid magnetic structure of claim 1, wherein the ferromagnetic pole is made of steel or vanadium pemendur.

11. The hybrid magnetic structure of claim 1, wherein the blocks of permanent magnet material comprise a rare earth element.

12. The hybrid magnetic structure of claim 11, wherein the blocks of permanent magnet material comprise neodymium iron boron or samarium cobalt.

13. The hybrid magnetic structure of claim 1, further comprising an upper interface attached on top of the hybrid magnetic structure.

14. The hybrid magnetic structure of claim 1, further comprising a retainer rod running through the structure orthogonal to the height of the ferromagnetic pole.

15. The hybrid magnetic structure of claim 1, further comprising a lower locator plate attached to the bottom of the hybrid magnetic structure.

16. The hybrid magnetic structure of claim 1, further comprising a field adjustment element assembled beneath a selected ferromagnetic pole, wherein said field adjustment element comprises a lower block of permanent magnet material whose magnetization orientation is facing into or out of said pole such that the magnetization orientations of all blocks of permanent magnet material around each pole piece are uniformly facing either out of or into the pole.

17. The hybrid magnetic structure of claim 1, further comprising a protective cover.

* * * * *